United States Patent
Fernandez Lopez et al.

(10) Patent No.: US 8,623,636 B2
(45) Date of Patent: Jan. 7, 2014

(54) NANOPARTICLE BIOSENSOR, METHOD OF PREPARING SAME AND USES THEREOF

(75) Inventors: Victor Manuel Fernandez Lopez, Madrid (ES); Jose Angel Martin Gago, Madrid (ES); Marcos Pita Martinez, Madrid (ES); Jose Carlos Serna Pereda, Madrid (ES); Carlos Briones Llorente, Madrid (ES); Cristina Vaz Dominguez, Madrid (ES); Eva Mateo Marti, Madrid (ES)

(73) Assignees: Consejo Superior de Investigaciones Cientificas (ES); Instituto Nacional de Tecnica Aerospacial (ES)

( * ) Notice: Subject to any disclaimer, the term of this patent is extended or adjusted under 35 U.S.C. 154(b) by 693 days.

(21) Appl. No.: 12/067,166

(22) PCT Filed: Sep. 12, 2006

(86) PCT No.: PCT/ES2006/070134
§ 371 (c)(1),
(2), (4) Date: Mar. 10, 2010

(87) PCT Pub. No.: WO2007/034021
PCT Pub. Date: Mar. 29, 2007

(65) Prior Publication Data
US 2013/0040292 A1 Feb. 14, 2013

(30) Foreign Application Priority Data
Sep. 16, 2005 (ES) .................................. 200502269

(51) Int. Cl.
*C12Q 1/68* (2006.01)
*C12M 1/34* (2006.01)
*B05D 7/00* (2006.01)
*G01N 33/553* (2006.01)

(52) U.S. Cl.
USPC ........ 435/287.2; 435/6.1; 435/6.11; 427/214; 436/526; 536/23.1; 977/704

(58) Field of Classification Search
USPC ........ 435/6.1, 6.11, 287.2; 427/214; 436/526; 536/23.1; 977/704
See application file for complete search history.

(56) References Cited

U.S. PATENT DOCUMENTS 5,445,971 A 8/1995 Rohr
6,219,137 B1 * 4/2001 Vo-Dinh ....................... 356/301

(Continued)

FOREIGN PATENT DOCUMENTS

EP 1138743 A1 10/2001
WO WO03072247 * 9/2003

(Continued)

OTHER PUBLICATIONS

Stoeva et al, Three-Layer Composite Magnetic Nanoparticle Probes for DNA, 2005, JACS, 127, 15362-15363.*

(Continued)

*Primary Examiner* — Dave Nguyen
*Assistant Examiner* — Narayan Bhat
(74) *Attorney, Agent, or Firm* — Cantor Colburn LLP

(57) ABSTRACT

The invention relates to the field of biosensors and, more specifically, to nanoparticle biosensors comprising: a magnetic core, a silica layer, one or more outer metal layers which can be of different types and deposited in an alternating manner and immobilized on the outer surface, and a layer of synthetic or natural organic or inorganic biosensor molecules that can bind to biomolecules. The invention also relates to a method of obtaining the nanoparticle biosensors as well as to the different uses thereof.

23 Claims, 3 Drawing Sheets

(56) References Cited

U.S. PATENT DOCUMENTS

2005/0048570 A1  3/2005  Weber et al.
2006/0105170 A1* 5/2006  Dobson et al. ............... 428/403

FOREIGN PATENT DOCUMENTS

WO    WO2004/021370    *  3/2004
WO    2005015213 A1       2/2005

OTHER PUBLICATIONS

Stoeva et al, Suporting information, Three-Layer Composite Magnetic Nanoparticle Probes for DNA, 2005, JACS, 127, pp. 1-11.*
Famulok et al, Nucleic Acid Aptamers From Selection in Vitro to Applications in Vivo, 2000, Acc. Chem. Res. 33, 591-599.*
Yoon et al, Multifunctional Nanoparticles Possessing A "Magnetic Motor Effect" for Drug or Gene Delivery, 2005, Angew. Chem. 117, 1092-1095.*
Endo et al, Localized surface plasmon resonance based label-free optical biosensor for monitoring Peptide Nucleic Acid-DNA hybridization, 2005, Proceedings of 2005 5th IEEE Conference on Nanotechnology, Nagoya, Japan, Jul. 2005, pp. 1-4.*
J. Mater. Chem., vol. 15, Jun. 2005, pp. 2095-2098.
Technical Report of The Institute of Electronics, Information and Communication Engineers, MBE, vol. 101, No. 182, 2001, pp. 93-99, Abstract.
Watson et al., "Molecular Structure of Nucleic Acids: A Structure for Deoxyribose Nucleic Acid", Nature, vol. 171, No. 4356, 1953, pp. 737-738.
Wittung et al., "DNA-like double helix formed by peptide nucleic acid", Letters to Nature, vol. 368, 1994, pp. 561-563.
Yeni et al., "Antiretroviral Treatment for Adult HIV Infection in 2002: Updated Recommendations of the international AIDS Society—USA Panel", JAMA, vol. 288, No. 2, 2002, 1 page, Abstract Only.
Zhu et al., "DNA Hybridization at Magnetic Nanoparticles with Electrochemical Stripping Detection", Electroanalysis, 16, No. 23, 2004, pp. 1925-1930.
Abad et al., "Immobilization of Peroxidase Glycoprotein on Gold Electrodes Modified with Mixed Epoxy-Boronic Acid Monolayers", J. Am. Chem. Soc. 124, 2002, pp. 12845-12853.
Arlinghaus et al., "Analysis of Biosensor Chips for Identification of Nucleic Acids", Anal. Chem. 69, 1997, pp. 3747-3753.
Arlinghaus et al., "Genome diagnostics with TOF-SIMS", Applied Surface Science 203-204, 2003, pp. 689-692.
Brandt et al., "PNA microarrays for hybridisation of unlabled DNA samples", Nucleic Acids Research, vol. 13, No. 19 e119, 2003, 9 pages.
Briones et al., "Ordered Self-Assembled Monolayers of Peptide Nucleic Acids with DNA Recognition Capability", Physical Review Letters, vol. 93, No. 20, 2004, pp. 208103-1 to 208103-4.
Briones et al., "Structural and functional characterization of self-assembled monolayers of peptide nucleic acids and its interaction with complementary DNA", Journal of Molecular Catalysis A: Chemical 228, 2005, pp. 131-136.
Del Monte et al., "Formation of y-Fe2O3 Isolated Nanoparticles in a Silica Matrix", Langmuir 13, 1997, pp. 3627-3634.
Demidov et al., "Kinetics and mechanism of polyamide ("peptide") nucleic acid binding to duplex DNA", Proc. Natl. Acad. Sci. USA, vol. 92, 1995, pp. 2637-2641.
Demidov et al., "Kinetics and mechanism of the DNA double helix invasion by pseudocomplementary peptide nucleic acids", PNAS, vol. 99, No. 9, 2002, pp. 5953-5958.
Duff et al., "A New Hydrosol of Gold Clusters. 1. Formation and Particles Size Variation", Langmuir 9, 1993, pp. 2301-2309.
Egholm et al., "Peptide Nucleic Acids (PNA). Oligonucleotide Analogues with an Achiral Peptide Backbone", J. Am. Chem. Soc. 114, 1992, pp. 1895-1897.

Egholm et al., "PNA hybridizes to complementary oligonucleotides obeying the Watson-Crick hydrogen-bonding rules", Letters to Nature, vol. 365, 1993, pp. 566-568.
Garcell et al., "Interfacial and Rheological Characteristics of Maghemite Aqueous Suspensions", Journal of Colloid and Interface Science 205, 1998, pp. 470-475.
Griffin et al., "Genetic analysis by peptide nucleic acid affinity MALDI-TOF mass spectrometry", Nature Biotechnology, vol. 15, 1997, pp. 1368-1372.
Hacia, "Resequencing and mutational analysis using oligonucleotide microarrays", Nature Genetics Supplement, vol. 21, 1999, pp. 42-47.
Halas, "Playing with Plasmons: Tuning the Optical Resonant Properties of Metallic Nanoshells", MRS Bulletin, vol. 30, 2005, pp. 362-367.
Harris, "The DNA Microarray: The late 1980's were heady days for molecular biologists", The Scientist, 2005, 8 pages.
Huang et al., "Synthesis of Dumbbell-Shaped Au-Ag Core-Shell Nanorods by Seed-Mediated Growth under Alkaline Conditions", Langmuir 20, 2004, pp. 6089-6092.
Jackson et al., "Silver Nanoshells: Variations in Morphologies and Optical Properties", J. Phys. Chem. B, 105, 2001, pp. 2743-2746.
Jolivet et al., "Synthesis and Physicochemical Study of Non-Surfactant Magnetic Colloids in an Aqueous Medium", Nouv. J. Chim. 7, 1983, pp. 325-331 with English Abstract.
Kambhampati et al., "Investigating the kinetics of DNA-DNA and PNA-DNA interactions using surface plasmon resonance-enhanced fluorescence spectroscopy", Biosensors & Bioelectronics 16, 2001, pp. 1109-1118.
Lee et al., "Preparation of Ultrafine Fe3O4 Particles by Precipitation in the Presence of PVA at High pH", Journal of Colloid and Interface Science 177, 1996, pp. 490-494.
Lee et al., "Multifunctional Magnetic Gold Nanocomposites: Human Epithelial Cancer Detection via Magnetic Resonance Imaging and Localized Synchronous Therapy", Advanced Functional Materials, 18, 2008, pp. 258-264.
Li et al., "Amplifying the electrical hybridization signals of DNA array by multilayer assembly of Au nanoparticle probes", The Analyst. Jul. 2003, vol. 128, No. 7, pp. 917-923.
Madoz et al., "Functionalization of Gold Surfaces for Specific and Reversible Attachment of a Fused β-Galactosidase and Choline-Receptor Protein", J. Am. Chem. Soc. 119, 1997, pp. 1043-1051.
Martinez et al., "Evolution subverting essentiality: Dispensability of the cell attachment Arg-Gly-Asp motif in multiply passaged foot-and-mouth disease virus", Proc. Natl. Acad. Sci. USA vol. 94, 1997, pp. 6798-6802.
Massart et al., "Effect of some parameters on the formation of colloidal magnetite in alkaline-medium-yield and particle size control", J. Chem. Phys. 84, 1987, pp. 967-973 with English Abstract.
Massart, "Preparation of Aqueous Magnetic Liquids in Alkaline and Acidic Media", IEEE Transactions on Magnetics, vol. Mag-17, No. 2, 1981, pp. 1247-1248.
Nielsen et al., "Sequence-Selective Recognition of DNA by Strand Displacement with a Thymine-Substituted Polyamide", Science, New Series, vol. 254, No. 5037, 1991, pp. 1497-1500.
Nielsen, "Applications of peptide nucleic acids", Current Opinion in Biotechnology 10, 1999, pp. 71-75.
Nielsen, "Peptide Nucleic Acid Targeting of Double-Stranded DNA", Methods in Enzymology, vol. 340, 2001, pp. 329-340.
Oldenburg et al., "Nanoengineering of optical resonances", Chemical Physics Letters 288, 1998, pp. 243-247.
Osawa et al., "Surface-Enhanced Infrared Absorption of p-Nitrobenzoic Acid Deposited on Silver Island Films: Contributions of Electromagnetic and Chemical Mechanisms", J. Phys. Chem. 95, 1991, pp. 9914-9919.
Parinov et al., "DNA sequencing by hybridization to microchip octa- and decanucleotides extended by stacked pentanucleotides", Nucleic Acids Research, vol. 24, No. 15, 1996, pp. 2998-3004.
Written Opinion for International Application No. PCT/ES2006/070134, International Application Filing Date Dec. 9, 2006; Date of Mailing May 2, 2007, 7 pages.
Philipse et al., "Magnetic Silica Dispersions: Preparation and Stability of Surface-Modified Silica Particles with a Magnetic Core", Langmuir 10, 1994, pp. 92-99.

(56) References Cited

OTHER PUBLICATIONS

Relogio et al., "Optimization of oligonucleotide-based DNA microarrays", Nucleic Acids Research, vol. 30, No. 11 e51, 2002, 10 pages.

Rogers et al., "Site-directed recombination via bifunctional PNA-DNA conjugates", PNAS, vol. 99, No. 26, 2002, pp. 16695-16700.

Solinas et al., "Sol-Gel Formation of y-Fe2O3/SiO2 Nanocomposites", Acta Mater. 49, 2001, pp. 2805-2811.

Southern et al., "Detection of Specific Sequences Among DNA Fragments Separated by Gel Electrophoresis", J. Of Mol. Biol. 98, 1975, pp. 503-517, PowerPoint Presentation.

Southern et al., "Arrays of complementary oligonucleotides for analysing the hybridisation behaviour of nucleic acids", Nucleic Acids Research, vol. 22, No. 8, 1994, pp. 1368-1373.

Sugimoto et al., "Formation of Uniform Spherical Magnetite Particles by Crystallization from Ferrous Hydroxide Gels", Journal of Colloid and Interface Science, vol. 74, No. 1, 1980, pp. 227-243.

Tartaj et al., "Single-Step Nanoengineering of Silica Coated Maghemite Hollow Spheres with Tunable Magnetic Properties", Advance Materials 13, No. 21, 2001, pp. 1620-1624.

Urakawa et al., "Preparation and Mossbauer spectroscopic characterization of ultrafine iron oxide particles", Journal of Materials Science Letters, 15, 1996, pp. 1237-1239.

Veintemillas-Verdaguer et al., "Continuous production of y-Fe2O3 ultrafine powders by laser pyrolysis", Materials Letters 35, 1998, pp. 227-231.

Vo-Dinh, "Surface-enchanced Raman spectroscopy using metallic nanostructures", Trends in Analytical Chemistry, vol. 17, No. 8 + 9, 1998, pp. 557-582.

Wagner et al., "Core shell particles consisting of cobalt ferrite and silica as model ferrofluids [CoFe2O4-SiO2 core shell particles]", Journal of Magnetism ad Magnetic Materials 252, 2002, pp. 4-6.

Wang et al., "Peptide Nucleic Acid Probes for Sequence-Specific DNA Biosensors", J. Am. Chem. Soc. 118, 1996, pp. 7667-7670.

Wang et al., "Mismatch-Sensitive Hybridization Detection by Peptide Nucleic Acids Immobilized on a Quartz Crystal Microbalance", Anal. Chem. 69, 1997, pp. 5200-5202.

Wang et al., "Sensitive electrochemical immunoassay for 2,4,6-trinitrotoluene based on functionalized silica nanoparticle labels", Analytica Chimica Acta 610, 2008, pp. 112-118.

\* cited by examiner

NANOPARTICLE BIOSENSOR, METHOD OF PREPARING SAME AND USES THEREOF

FIELD OF THE ART

The present invention relates to the field of biosensors, specifically to the use of peptide nucleic acid (PNA) probes immobilized on nanoparticles for detecting the hybridization of natural nucleic acids (DNA or RNA) of specific sequences. The nanoparticles are particularly formed by a magnetic core and an outer metal layer, on which the relevant probes with base sequences complementary to the target object of identification and detection are immobilized. The magnetic, electric and optical properties of the nanoparticles are used to improve the method, being focused on the magnetic, optical or electric signal difference obtained from said nanoparticles before and after the modification involved in a positive hybridization assay. The types of tests which the present invention relates to can also be carried out spectroscopically on macroscopic metal surfaces.

BACKGROUND OF THE INVENTION

The progress of science in genetics, genomics and biotechnology has been spectacular ever since Watson and Crick published the double helix structure of DNA in 1953 and the molecular biology era was thus inaugurated. One of the most extended analytical applications of DNA consists of detecting other DNA or RNA molecules with specific complementary sequences, given the binding specificity between nucleotides through their nucleotide bases, what is known as the Watson-Crick parity rule; adenine (A) with thymine (T), and guanine (G) with cytosine (C). Thus, a certain sequence formed by a certain number of nucleotides becomes unique inside the genome of one or more species, and said sequence can thus be used to detect and characterize the presence of the organism having it. Given the current technological development, it is even possible to detect the presence of an organism, strain or variant differing in only one nucleotide with respect to other variants, which allows distinguishing between two mutants of one and the same microorganism, for example.

The development of the technology of microarrays, also called chips or microchips (Southern et al., 1994; reviews in Nature Genetics 21, supplement, 1999; Harris, 2005), according to which thousands of molecular probes, mainly nucleic acids or proteins, can be covalently fixed to a solid support (glass, nitrocellulose, nylon, etc.), has entailed an important progress in the biotechnology field. Gene expression studies, nucleotide polymorphism (SNP) studies, microorganism typing and minisequencing can be carried out by means of DNA microarrays. This technique uses the experimental methodology developed by E. Southern (Southern, 1975), according to which nucleic acids (both long strands and short oligonucleotides) can be fixed to a solid support and form stable hybrids with their radioactively or fluorescently labeled complementary nucleic acids. The stability of the hybrids is determined by the degree of complementarity of the nucleotide sequences and by external factors such as the ionic strength of the medium, pH or temperature. (Parinov et al., 1996; Hacia, 1999; Relógio et al., 2002).

The use of molecules similar to natural nucleic acids for several applications has also been relevant in biotechnology. Within said molecules, the case of peptide nucleic acids (abbreviated as PNA), described for the first time by Nielsen et al. in 1991 (Nielsen et al., 1991), is particularly interesting. PNA consists of a polymer the backbone of which has a peptide nature, unlike the backbone of sugars and phosphates typical of natural nucleic acids (DNA and RNA). The PNA backbone is formed by N-(2-aminoethyl)glycine units joined by peptide bonds, it is achiral, electrically neutral and lacks phosphorus atoms (Egholm et al., 1992; Egholm et al., 1993). Purine (A and G) and pyrimidine (C and T) nucleotide bases are joined to the PNA backbone by means of methylene carbonyl bonds in a conformation such that they can interact exactly with the nucleotide bases of natural nucleic acids.

PNA is characterized by its capacity to hybridize stably and specifically with complementary DNA according to the Watson-Crick base parity rules (Egholm et al., 1993). In fact, single stranded PNAs (ssPNA) have greater affinity for complementary ssDNA than the ssDNA with a sequence identical to that of PNA. This is mainly due to the electrically neutral nature of PNA, preventing repulsion phenomena between strands present in DNA-DNA interaction (Nielsen et al., 1991; Wittung et al., 1994). The high affinity of PNA for DNA even allows hybridizing ssPNA to double stranded DNA (dsDNA) by means of a process called "strand invasion" (Demidov et al., 1995; Nielsen, 2001; Demidov et al., 2002) and allows using PNA probes to induce recombination and/or specific blocking of specific genes (Rogers et al., 2002). Furthermore, the interaction of PNA to DNA is very specific and for virtually all the base pairs which can be formed, the heat stability difference between correct and incorrect pairing is greater in a PNA-DNA duplex than in the DNA-DNA duplex (Egholm et al., 1993). Therefore, the temperature difference between that at which a complete pairing occurs and that in which one of the bases is unpaired is greater in the PNA-DNA case than in the DNA-DNA case. A biosensor based on immobilized PNA probes will thus be potentially more efficient than another biosensor based on DNA for detecting mutations and SNPs in a target nucleic acid molecule.

Given the structure of its artificial peptidomimetic backbone, PNA is not sensitive to the action of natural biodegrading enzymes such as DNases, RNases or proteases, therefore its biological stability is much greater than that of DNA or RNA. (Nielsen, 1999). Finally, the insensitivity of PNA to pH or ionic strength variations also makes it have a much greater chemical stability and offer greater experimental possibilities for its hybridization to different molecules in different medium compositions (Egholm et al., 1993; Kambhampati et al., 2001). Due to the foregoing, the exploitation of the physicochemical peculiarities of PNA for its use in systems for detecting and quantifying natural nucleic acids is evidently interesting.

Some of the physicochemical changes associated to PNA/DNA or PNA/RNA hybridization are obvious. One of them is the mass increase involved in this pairing; in this sense PNA/DNA(RNA) biosensors have been developed using a quartz crystal microbalance as a very sensitive instrument for detecting small mass changes occurring after the hybridization between complementary sequences (Wang et al., 1997) or mass spectroscopy in the MALDI-TOF modality (Griffin et al., 1997; Arlinghaus et al., 2003; Brandt et al., 2003).

Other systems for detecting the hybridization between a PNA probe and the DNA target have furthermore been developed which base the detection of hybridization on the appearance of a phosphorus signal, since this element is not present in the PNA strand but does form part of the target DNA (or RNA) strand backbone. This possibility has been shown by Arlinghaus et al. with the SIRIMP (Sputter-Initiated Resonance Ionization Microprobe Phosphorous Image) technique (Arlinghaus et al., 1997). Similar results have been obtained by the inventors of the present invention by using the X-ray photoemission spectroscopy (XPS) technique in PNA probes immobilized on planar plates with a gold surface, before and after the hybridization to complementary DNA targets. It has been observed by means of XPS that with hybridization (and after the corresponding washing in controlled conditions to prevent the non-specific binding of the target) there is an increase of between 2 and 4 times in the nitrogen signal (photoemission peak corresponding to N1s, normalized to the Au4f peak of the substrate), and the appearance of a phosphorus signal (P2p peak normalized to Au4f) which did not exist in PNA (Briones et al., 2004; Briones et al., 2005).

Conducting many of these assays in a homogeneous phase has a number of difficulties due to the fact that target DNA or RNA molecules are usually extremely diluted in natural samples, therefore the hybridization reaction is usually carried out on surfaces on which the PNA probe molecule has been previously immobilized. This represents a limitation of the assay because the amount of probe is limited to a layer of PNA molecules on the surface in question, with which the sample to be analyzed must necessarily be placed in contact in order to give a positive signal. The sensitivity and the detection limit of these techniques is therefore also limited.

At this point, the use of nanoparticles, and particularly magnetic nanoparticles, involves a very significant progress because a small amount of magnetic nanoparticles can be re-suspended in large sample volumes and can be subsequently recovered by means of applying an external magnetic field. It is thus possible to purify and/or pre-concentrate very minor and diluted amounts of the target DNA hybridizing specifically with the PNA immobilized on the nanoparticles, whereby the detection limit is reduced to a great extent. These types of systems allow determining the presence of specific DNA sequences of interest in situations in which an early detection thereof can be critical, for example for preventing harmful effects that the existence of the organism species or strains having said characteristic sequences may have. This fact has a great application in human and veterinary biomedicine, among others in the following aspects: i) detection of viral, bacterial, fungal or protozoan type pathogens; ii) characterization of mutations or genetic polymorphisms (SNPs) in said agents which can make them resistant to drugs or facilitate their escape from the immune system or to vaccines; iii) characterization of mutations or SNPs in human or animal genes, related to diseases or prone to them; iv) detection of specific tumor markers. This detection potential likewise has important applications in food and environmental control, in aspects including the following: i) detection of specific microorganisms, pathogens or contaminants; ii) detection of the presence of transgenic or genetically manipulated organisms (GMOs), being able to quantify if their presence is above the allowed limits. In all these cases, a considerable sample volume can be analyzed using hardly a few micrograms of nanoparticles in suspension, which are subsequently concentrated by means of an external magnetic field. It is thus possible to increase the sensitivity of the detection by several orders of magnitude.

Ferrofluids, which are stable ferromagnetic or ferromagnetic nanoparticle suspensions with a narrow particle size distribution, are particularly interesting for the analytical applications contemplated in this invention patent. These types of nanoparticles were initially obtained by means of mechanically grinding iron oxide samples with magnetic properties. However, this method, in addition to being expensive and slow, causes a high size distribution in the particles obtained. The alternative arose with co-precipitation methods, in which dissolved salts with the suitable ions (for example, $Fe^{2+}$ and $Fe^{3+}$ in a 1:2 ratio) are used and are taken to conditions in which said solution becomes unstable and the desired solid precipitates (in the same example, precipitation is achieved by taking the solution to 1M NaOH to boiling). These methods produce nanoparticles that are small enough to have superparamagnetism. This phenomenon involves that in one particle, due to its miniscule size, there is only one permanent magnetic domain, but with the capacity to rotate. Consequently, in a ferrofluid the magnetic moment of each nanoparticle is oriented at random and they cancel each other out, such that in the absence of an external field the fluid behaves as if it were not a magnetic solid. When these nanoparticles are subjected to a magnetic field, either by rotation inside the solution or by orientation of their magnetic field, they are oriented according to the external field. This causes a strong particle-particle attraction that is transmitted throughout the fluid. Although the possibility that the particles are concentrated through the application of an external magnetic field is obviously interesting, it is not desirable for the magnetic interactions to be so strong as to favor a collective orientation, and a possible aggregation and coagulation.

Therefore, to obtain a stable ferrofluid under a moderately strong magnetic field, i.e., that the force of attraction between particles is less than thermal energy associated to the particles, the latter must be very small. For the magnetic single-domain typical of superparamagnetism to appear, the upper limit of the particle size admitted at room temperature is about 3 nm for iron, and about 10 nm for $Fe_3O_4$ (magnetite) and for its oxidized form 3-$Fe_2O_3$ (maghemite). In the case of $CoFe_2O_4$ (cobalt ferrite), the particle size can reach up to 20 nm. Above these limits, particles that are too large can act as aggregation nuclei and grow, destabilizing the suspension. It is clear obvious that a small particle size and a narrow size distribution within the particle population are necessary. With these characteristics, ferrofluids are formed by stable phases of materials which can be moved or controlled by magnetic gradients. The three mentioned oxides, if they are synthesized in a suitable and coherent size, have a high applicability for these purposes.

The main direct method of obtaining magnetic nanoparticles of magnetite in solution, with a narrow size distribution, starts from iron salts (Massart, 1981). Magnetic nanoparticles can also be synthesized by means of vapor methods such as laser pyrolysis (Veintenillas et al., 1998), giving rise to very dispersed particles with a very small magnetic saturation, or the flame method (Urakawa et al., 1996) generating polydispersed particles. A silica matrix has also been used to obtain magnetic nanoparticles but the size distribution is too wide (del Monte et al., 1997).

Several synthesis methods for obtaining spherical magnetite nanoparticles in solution are currently known. According to one of said systems, a ferric hydroxide suspension is partially oxidized with different oxidizing agents. Spherical magnetite nanoparticles with a narrow size distribution for ranges selected from the limits 30 to 1100 nm have been obtained mixing $FeSO_4$ with KOH in the presence of nitrate ion and taking the resulting gel to 90° C. for several hours (Sugimoto and Matijevic, 1980). However, the application of this method is limited because magnetite nanoparticles with diameters greater than 30 nm are no longer superparamagnetic.

Nevertheless, as has been indicated, the main method of obtaining spherical nanoparticles is the Massart method, consisting of aging a mixture of ferrous and ferric hydroxide solutions in an aqueous medium (Massart and Cabuil, 1987). Particles that are very homogeneous in size and chemical composition are obtained with a $Fe^{2+}/Fe^{3+}$ stoichiometry=0.5. It has furthermore been observed that, adjusting the pH and the ionic strength of the precipitation medium, the average particle size can be controlled in an order of magnitude within the nanometer range (between 1.6 and 12.5 nm) (Jolivet et al., 1983), such that the particle size decreases as the pH and the ionic strength increase. Both factors determine the isostatic change of the surface of the particles and consequently, the chemical composition of the surface.

In one of the descriptions for preparing this material, spherical magnetite particles between 8 and 14 nm were obtained by varying the nature of the base used in the precipitation ($NH_4OH$, NaOH or KOH) and the temperature. To precipitate these particles, 50 ml of an aqueous 0.33 M $FeCl_2$ and 0.66 M $FeCl_3$ solution were added to 450 ml of a basic 1 M solution with strong stirring. A $N_2$ gas flow was previously passed through the basic solution to ensure that the final precipitate was formed by magnetite only. The smallest particles were obtained by adding a 1 M KOH solution with 1% by weight of poly(vinyl alcohol) (PVA) to the mixture of iron salts at room temperature (Lee et al., 1996).

A method similar to the Massart method is used to synthesize $CoFe_2O_4$ nanoparticles, in which $Fe^{2+}$ is changed for $Co^{2+}$ and another one of the experimental conditions, such as the temperature for adding reagents to the basic medium, is changed. The process is similar to the magnetite method already mentioned above (Wagner et al., 2002).

The magnetic particles with a suitable size synthesized by the previous methods have an isoelectric point close to 7 for magnetite and of 9 in the case of cobalt ferrite, which makes them very unstable in aqueous solution at neutral pHs; certain aggregation is already observed at pH values±2 units of the isoelectric point, and they precipitate at pH values±1.5 units. For this reason, it is necessary to coat them with a compound stabilizing the suspension in water at pH values close to neutrality. This coating can be of different kinds: polymers, organic substances, or different metals or oxides. A great stability against aggregation is achieved in the event of coating particles with a silica layer, magnetic attractions and Van der Waals interactions occurring between said nanoparticles being reduced. A high resistance against heat treatments is furthermore provided (Tartaj et al., 2001). A problem involved with the silica coating is the low mechanical strength that said layer has inside a stirring tank. In addition, this silica coating could occur not on individual nanoparticles but on aggregates of about five nanoparticles (Philipse et al., 1994). On the contrary, the presence of said silica layer offers several advantages in addition to their stabilization at neutral pH, such as for example the possibility of modifying their surface by adding functional groups existing in silane type bond molecules. These molecules have a trialkoxysilane group at one of their ends, and a short chain with the relevant functional group (amino, mercapto, hydroxide, epoxide, etc) at the end of the chain comes out of the free bond of the silicon. Thus, instead of having the nanoparticles in a closed silica layer, they can be chemically modified to create the desired functionalized surface.

Thus, a modification with an outer gold layer has been carried out on silica nanoparticles (Oldenburg et al., 1998). To that end, the silica surface is silanized with 3-aminopropyltriethoxysilane, such that multiple amino groups are incorporated on the surface. Previously synthesized gold nanoparticles are immobilized on these groups and a subsequent growing step is carried out reducing gold (III) ions until desired, the gold layer on the silica being closed.

This outer metal layer (preferably gold or silver) adds many other properties to the silica-coated magnetic nanoparticles among which providing a singular optical property, the surface plasmon phenomenon, is worth emphasizing in relation to the present invention.

However, nanoparticles having all the previously described properties and the viability of their use as a support for detecting hybridization between complementary organic molecules and their application in the development of new tools or technological platforms in nanobiotechnology are not known.

BRIEF DESCRIPTION OF THE INVENTION

A first aspect of the invention relates to a nanoparticle biosensor comprising: a magnetic nanoparticle, a silica layer, one or more outer metal layer or layers which can be of different types and deposited in an alternating manner and immobilized on its outer surface, and a layer of synthetic or natural organic or inorganic biosensor molecules that can bind to biomolecules. The nanoparticle biosensor of the invention preferably comprises a magnetic nanoparticle with a diameter thickness between 4-30 nm, a silica layer with a thickness between 1-20 nm, a metal layer with a thickness between 1-200 nm and a layer of synthetic or natural organic or inorganic biosensor molecules that can bind to biomolecules.

A second aspect of the invention relates to the method of preparing the nanoparticle biosensor of the invention comprising the steps of preparing a colloid of magnetic particles with a size between 4-20 nm; conditioning a colloid so that it is stable at basic pHs (greater than pH=7); coating the colloidal nanoparticles in a basic medium with a silica layer with a thickness between 1-20 nm; chemically functionalizing the surface of the silica-coated magnetic nanoparticles of the previous step with a metal layer and immobilizing the organic biosensor molecule on the surface of the resulting nanoparticle.

A third aspect of the present invention relates to the different applications of the nanoparticle biosensors of the present invention.

A fourth aspect of the invention relates to methods for determining the hybridization or binding of a biological molecule to the organic or inorganic biosensor molecule immobilized on a nanoparticle biosensor of the invention. Said methods preferably are but are not limited to: spectroscopic detection methods using visible or infrared radiation, or Raman spectrosocopy, or XPS, or electrochemical detection methods.

Other aspects of the present invention will be evident for a person skilled in the art in view of the description of the invention.

DETAILED DESCRIPTION OF THE INVENTION

Figure 1:
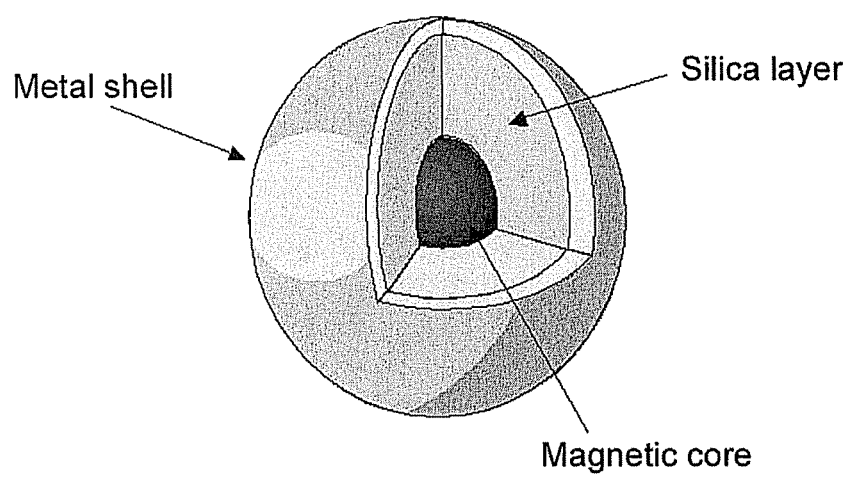
FIG. 1.—Diagram of the nanoparticle biosensor, indicating its different layers.

The present invention deals with the problem of providing new tools for identifying and characterizing biomolecules, and more specifically new biosensors which can bind to nucleic acids with high sensitivity and specificity.

The invention is based on the fact that the inventors have observed that it is possible to identify the hybridization occurring between natural nucleic acids (DNA or RNA) and molecules similar to them (more specifically, PNA) when these PNA probes are immobilized on the metal surface of nanoparticles with a magnetic core.

Any type of organic or inorganic molecule can be immobilized on the surface of these magnetic nanoparticles coated with a metal layer thanks to the properties of said surfaces, provided that such molecule includes functional groups which can accept electronic density, such as amino groups or thiol groups (see Example 1). The immobilized molecules can or cannot give rise to arrangements in the form of self-assembled monolayers (SAMs), in which case an optimal packing density is obtained. The formation of SAMs occurs, for example, in the case of immobilization of thiolated PNAs on gold surfaces.

The new magnetic, electrical and optical properties—which are integrated and complement one another—of the nanoparticles with the organic or inorganic molecule immobilized on its surface can thus be used to develop specific biosensors. Firstly, the magnetic surface core allows said particles to be captured by an external magnetic field and allows concentrating the analyzed sample when it is at low concentrations. Secondly, it is possible to analyze (see Example 2 and 3) the optical signal difference caused by said nanoparticles with a biosensor molecule immobilized on its surface, before and after the hybridization of a complementary nucleic acid present in a test biological sample.

The metal used as an outer layer further provides a singular optical property: the surface plasmon phenomenon. This phenomenon consists of the collective vibration of the electrons of the metal surface, causing an absorption band located in the ultraviolet-visible region (characteristic of the metal and of the size of the nanoparticles) at the wavelength in which the resonance condition in said electrons occurs. The surface plasmon phenomenon also has consequences in the chemical bond vibration energy region, causing the Surface Enhancement Raman Spectroscopy (SERS) (Vo-Dinh, 1998) and Surface Enhancement InfraRed Absorption (SEIRA) (Osawa et al., 1991) effects. These effects cause a considerable increase in certain vibration modes of the molecules located on the metal surfaces, which in the case of SERS can reach up to $10^6$ times, whereas in SEIRA it can reach an increase of $10^2$ times. These optical signal increase effects fundamentally depend on the material causing them (Au, Ag, Cu), on the thickness of the layer and its outer roughness and also on the thickness (in the case of sheets) or on the diameter of the particle (in the case of nanoparticles) and can be measured by spectroscopy techniques.

Finally, another property provided by the metal surface is its ease for acting as a support for self-assembled monolayers, especially for thiolated groups on gold surfaces (Madoz et al., 1997; Madoz-Gúrpide et al., 2000; Abad et al., 2002; Briones et al., 2004).

Therefore, a first aspect of the present invention is formed by a nanoparticle biosensor comprising:
   a) a magnetic nanoparticle
   b) a silica layer
   c) one (or more) outer metal layer (s), which can be of different types and deposited in an alternating manner and immobilized on its outer surface
   d) a layer of synthetic or natural organic or inorganic biosensor molecules which can bind to biomolecules.

The term "nanoparticle biosensor" as used in the present invention relates to particles with a size comprised between 5 and 250 nanometers (nm), preferably between 50 and 100 nm and more preferably of 60 nm further comprising all the previously described characteristics.

The size of the nanoparticle can vary according to the thickness of the different layers described previously, which by way of description, can vary as follows:
   i) a magnetic particle between 4 and 30 nm and
   ii) a silica layer with a thickness between 1 and 20 nm and
   iii) a metal layer with a controlled thickness between 1 and 200 nm Maghemite (3-$Fe_2O_3$) and magnetite ($Fe_3O_4$) have permanent magnetic properties among the numerous existing iron oxides (Garcell et al., 1998; Solinas et al., 2001). In addition, nanoparticles of cobalt ferrite ($CoFe_2O_4$), a compound with the same inverse spinel structure typical of magnetite in which cobalt has substituted iron with oxidation state II, can be used. Another example of magnetic material alternative to those described is iron-platinum (FePt), although it is not an oxide.

Therefore, as used in the present invention the term "magnetic nanoparticle" relates to an oxidixed or unoxidized magnetic material belonging, by way of illustration and without limiting the scope of the present invention, respectively, to one of the following groups or to any combination thereof:
   i) iron oxide, such as magnetite ($Fe_3O_4$) and its oxidized form maghemite (3-$Fe_2O_3$) or a cobalt-iron oxide such as cobalt ferrite ($CoFe_2O_4$) or
   ii) non-oxide magnetic materials such as iron-platinum-(FePt);

As used in the present invention the term "outer metal layer" relates to metals inducing the spectroscopic signal increase and belonging, by way of illustration and without limiting the scope of the invention, to the following group: gold (Au), silver (Ag), copper (Cu), platinum (Pt) or an alloy formed by several or all these metals.

As used in the present invention the term "biosensor molecules" relates to an organic or inorganic biological molecule or molecule similar to a biological molecule, immobilized on a nanoparticle acting as a physical support, which can specifically bind or hybridize to other biological molecules or analogs thereof such that the binding process can be tracked. Said biological molecules or biological molecule analogs further include a functional group which can accept electronic density involving its chemisorption or physisorption, belonging by way of illustration and without limiting the scope of the present invention to the following list: amino groups, thiol groups, epoxy groups, disulfide groups, dialkyl sulfides, as well as amine and alcohols in platinum. The molecules having said functional groups, both in the structure itself of the molecule and due to the effect of the synthetic addition of said group synthetically, can be selected, by way of illustration and without limiting the scope of the present invention, from one of the following groups:

a) natural biomolecules: single or double stranded nucleic acids (DNA or RNA), enzymes, antibodies, membrane proteins, heat shock proteins, chaperonins, other proteins, monosaccharides, polysaccharides, glycoproteins, fatty acids, terpenes, steroids, other molecules of a lipid nature, lipoproteins, hormones, vitamins, metabolites, hydrocarbons, natural molecules with antibiotic or antiviral activity, or macromolecular aggregates formed by proteins and/or nucleic acids or other combinations of the previously mentioned molecules;

b) natural biomolecules obtained by in vitro selection processes: aptamers, ribozymes or aptazymes;

c) artificial biomolecules: PNAs, other analogs of natural nucleic acids, natural and artificial nucleic acid chimers, polymers with the capacity to recognize shapes ("molecular imprinted polymers" or MIPs), artificial antibodies, recombinant antibodies, mini-antibodies or synthetic molecules with antibiotic or antiviral activity.

As used in the present invention the term "hybridization" relates to the interaction between two complementary strands of natural nucleic acids or their artificial analogs, or generically, to the specific interaction between two proteins, an antibody and the antigen recognizing it, or a binding protein and its ligand.

The nanoparticles of the present invention can also be used in different biosensor formats based on the molecular recognition between antigen-antibody, receptor-ligand, enzyme-substrate or enzyme-inhibitor, in which the molecular recognition event gives rise to changes in optical and/or electric properties of the system which can be detected due to the composition and structure of the nanoparticles object of this invention; ultraviolet, visible or infrared spectroscopy; Raman spectroscopy and Surface Enhanced Raman Spectroscopy (SERS), Raman microscopy; transmission infrared, including FTIR and infrared microscopy; Surface Enhanced InfraRed Absorption (SEIRA) and Attenuated Total Reflection Spectroscopy" (ATR); techniques based on X-rays, XPS, NEXAFS, XANES.

As used in the present invention, the term "nucleic acid" relates to a deoxyribonucleic acid (DNA), ribonucleic acid (RNA) or peptide nucleic acid (PNA) sequence, with a length equal to or greater than 2 nucleotides (DNA or RNA) or 2 nucleotide bases bonded to their corresponding backbone (PNA) (abbreviated as nt) which can be single stranded or double stranded.

As used in the present invention the term "peptide nucleic acid (PNA)" relates to a molecule that is structurally similar to DNA in which the structural backbone is a polymer with a peptide nature formed by polymerization of N-(2-aminoethyl)glycine, to which the nucleic bases are joined by means of methylene carbonyl bonds.

As used in the present invention the term "recombinant antibodies" or "mini-antibodies" relates to fragments derived from antibodies constructed by recombinant DNA technology and which, despite their smaller size, conserve the antigen binding capacity because they maintain at least one invariable immunoglobulin domain (Fab) in which the antigen binding areas reside. Mini-antibodies can belong, by way of illustration and without limiting the scope of the invention, to the following group: Fab, F(ab')2, scFv, and recombinant single-domain antibodies. In the context of the present invention, recombinant single-domain antibodies and/or immunoglobulin type domains with independent binding and recognition capacity are understood as heavy chain variable domains (VH), as light chain variable domains (VL), as recombinant camelid antibodies (VHH), the humanized recombinant camelid antibodies, recombinant antibodies of other camelized species, IgNAR single-domain antibodies of cartilaginous fish; i.e. both domains that are naturally single-domain (such as VHH and IgNAR) and antibodies that have been altered by genetic engineering that can interact by themselves with the antigen and improve their stability and solubility properties are included.

One particular embodiment of the invention is formed by the nanoparticle biosensor of the invention in which the magnetic nanoparticle is formed by cobalt ferrite, the silica layer is functionalized with amino groups and thiol groups, the metal layer is made of gold and the immobilized biomolecule is a PNA modified at one of its ends, said modification consisting of inserting a thiol group in said end (see Example 1.1).

Another particular embodiment of the present invention is formed by the nanoparticle biosensor in which the magnetic nanoparticle is made of cobalt ferrite, the silica layer is functionalized with amino groups and thiol groups and the metal layer is formed by a silver layer and successively another gold layer, and the immobilized biomolecule is a PNA modified at one of its ends, said modification consisting of inserting a thiol group in said end (see Example 1.4).

In another particular aspect of the invention, the nanoparticle biosensor can be a mass nanoparticle biosensor, i.e., not have a magnetic core or silica layer and be formed only by a metal core.

A second aspect of the present invention is formed by the method of obtaining the nanoparticle biosensors of the invention, hereinafter method of the invention, comprising the steps of:

a) preparing a colloid of magnetic particles between 4 and 30 nm
b) conditioning the colloid so that it is stable at basic pHs (greater than pH=7),
c) coating the colloidal nanoparticles in a basic medium with a silica layer with a thickness between 1 and 20 nm,
d) chemically functionalizing the surface of the nanoparticles obtained in step c) in order to introduce functional groups,
e) coating the functionalized magnetic nanoparticles of step d) with a metal layer, comprising the steps of:
   e.i) synthesizing water-stable metal nanoparticles with a diameter between 3 and 20 nm
   e.ii) chemisorbing the metal nanoparticles on the resulting nanoparticles of the previously mentioned step d.
   e.iii) growing a metal layer on the product obtained in e.ii), forming a layer with a controlled thickness between 1 and 200 nm
f) immobilizing the biosensor molecule on the surface of the resulting nanoparticle of step e).

A preferred aspect of the present invention is formed by the method of the invention in which the magnetic particle is formed, by way of illustration and without limiting the scope of the invention, by the following groups of oxidized or unoxidized magnetic materials, respectively, or by any combination thereof:

i) iron oxide, such as magnetite ($Fe_3O_4$) and its oxidized form maghemite ($3\text{-}Fe_2O_3$), or a cobalt-iron oxide such as cobalt ferrite ($CoFe_2O_4$),
ii) non-oxide magnetic materials such as iron-platinum (FePt).

In said method, the iron and cobalt oxide is preferably cobalt ferrite (see Example 1), magnetite ($Fe_3O_4$) or its oxidized form ($3\text{-}Fe_2O_3$).

A more preferred aspect of the invention is formed by a method of the invention in which the conditioning of step b) of the method of the invention is carried out with tetramethylammonium hydroxide.

A still more preferred aspect of the present invention is formed by a method of the invention in which the silica coating of step c) of the method of the invention is carried out by treatment with a sodium silicate solution.

In addition, the thickness of the silica layer of the step c) of the method of the invention can vary according to the size of the desired nanoparticles. Thus, another embodiment of the present invention is formed by a method of the invention additionally comprising the following step:

c2) an extension of step c) after the treatment with sodium silicate, favoring the additional growth of the silica layer with tetraethoxyorthosilicate.

A preferred embodiment of the present invention is formed by the method of the invention in which the chemical functionalization of the surface of step d) of the method of the invention is carried out with a trialkoxysilane type reagent belonging, by way of illustration and without limiting the scope of the present invention, to the following group of compounds: 3-aminopropyl triethoxysilane, 3-mercaptopropyl trimethoxysilane or a mixture of both. Preferably, generally any trialkoxysilane type molecule can be introduced or different molecules with this structure can be simultaneously introduced, thus obtaining the desired functionalization.

Another particular embodiment of the method of the invention is formed by a method in which the metal layer of e) of the method of the invention is prepared from a metal belonging, by way of illustration and without limiting the scope of the invention, to the following group: gold (Au), silver (Ag), copper (Cu) or platinum (Pt), or an alloy formed by several or all these metals, Au/Ag or Au/Cu, for example.

In another particular embodiment of the method of the invention, the metal nanoparticles of step e.i) are gold nanoparticles which are prepared by reducing $HAuCl_4$ dissolved in basic water with tetrakis(hydroxyphenyl)phosphonium chloride.

In yet another particular embodiment of the method of the invention, to cause the chemisorption of step e.ii), the nanoparticles of step d) are mixed with those of step e), such that there is an excess of metal nanoparticles.

In another preferred embodiment of the method of the invention, the growth of a gold layer mentioned in step e.iii) of the method of the invention is carried out by successive-step reduction on the nucleation seeds of $Au^{3+}$ with hydroxylamine hydrochloride.

In another particular embodiment of the method of the invention, the growth of a gold layer mentioned in step e.iii) of the method of the invention is carried out by successive-step reduction on the nucleation seeds of $Au^{3+}$ with formaldehyde.

In another still more preferred embodiment of the method of the invention, the growth of a metal layer of step e.iii) of the method of the invention consists of generating a gold/silver alloy which is carried out by successive-step reduction on nucleation seeds of $Ag+$ with formaldehyde in the presence of ammonia (see Example 1.2).

Another particular object of the invention is formed by the method of the invention in which the immobilized biosensor molecule in step f) of the method of the invention belongs, by way of illustration and without limiting the scope of the present invention, to one of the following groups:

a) natural biomolecules: single or double stranded nucleic acids (DNA or RNA), enzymes, antibodies, membrane proteins, heat shock proteins, chaperonins, other proteins, monosaccharides, polysaccharides, glycoproteins, fatty acids, terpenes, steroids, other molecules of a lipid nature, lipoproteins, hormones, vitamins, metabolites, hydrocarbons, natural molecules with antibiotic or antiviral activity, or macromolecular aggregates formed by proteins and/or nucleic acids or other combinations of the previously mentioned molecules;

b) natural biomolecules obtained by in vitro selection processes: aptamers, ribozymes or aptazymes;

c) artificial biomolecules: PNAs, other analogs of natural nucleic acids, natural and artificial nucleic acid chimers, polymers with the capacity to recognize shapes ("molecular imprinted polymers" or MIPs), artificial antibodies, recombinant antibodies, mini-antibodies or synthetic molecules with antibiotic or antiviral activity.

As mentioned above, said biosensor molecule includes a functional group, both in the structure itself of the molecule and due to the effect of the synthetic addition of said group, which can accept electronic density, belonging, by way of illustration and without limiting the scope of the present invention, to the following list: amino groups, thiol groups, disulfide groups, dialkyl sulfides, epoxy groups, as well as amines and alcohols in platinum.

Another particular aspect of the invention is formed by the method of the invention in which the immobilized biomolecule in the step f) of the method of the invention is a peptide nucleic acid (PNA) molecule.

Given the characteristics of these immobilized biosensor molecules it is possible to achieve that, in controlled hybridization and washing conditions, the biosensor molecules, PNA molecules for example, hybridize only with their perfectly complementary DNA strands. This detection specificity can be high enough to discriminate between two target DNA molecules differing in a single mutation or genetic polymorphism (SNP). Therefore, such immobilized biomolecules can detect the existence of DNA strands in a sample by using suitable methods, which allows their application in different industrial sectors, mainly in human and veterinary biomedicine, food and environmental control.

Therefore a third aspect of the present invention is formed by the use of the different applications of the nanoparticle biosensor of the invention, by way of illustration, in at least one of the following aspects:

i) detection of viral, bacterial, fungal or protozoan type pathogens,
ii) characterization of mutations or genetic polymorphisms (SNPs) in said agents which can make them resistant to drugs or facilitate the escape from vaccines,
iii) characterization of mutations or SNPs in human or animal genes, related to diseases or prone to them,
iv) detection of specific tumor markers.
v) detection of specific microorganisms, pathogens or contaminants in food, and
vi) detection of microorganisms or toxins contaminating the environment.

In addition, the nanoparticle biosensors of the present invention can also be used to prepare a microarray or micrometric in which each point of the microarray can be formed by a nanoparticle biosensor of the present invention directed at a certain biological element (a nucleic acid with a certain sequence, for example). The parallel analysis of a cluster of different hybridizations caused on as many other types of nanoparticle biosensors would thus be possible. Thus, another particular object of the present invention is formed by a biosensor device formed by a series of nanoparticle biosensors of the present invention arranged on a micromatrix or microarray type surface.

A fourth aspect of the present invention is formed by an assay for determining the hybridization, binding or interaction of a biological molecule to the molecule immobilized in a nanoparticle biosensor of the invention, hereinafter hybridization determination assay of the invention, comprising the following steps:
  i) reacting the nanoparticle biosensor of the invention with a sample which can contain the candidate biological sample, which can have or not have the sequences complementary to the immobilized organic biomolecule, in suitable conditions for its hybridization,
  ii) capturing the nanoparticle biosensors by magnetic sedimentation, and
  iii) determining the hybridization, or not, occurred in i).
  iv) deducing the existence, or not, of the candidate biological molecule in the sample which can contain it and where appropriate, deducing the sequence of such candidate biological molecule according to its degree of hybridization with the nanoparticle biosensor.
  v) optionally quantifying the concentration of the candidate biological molecule in the sample.

As mentioned previously, a particular embodiment of the invention is a nanoparticle biosensor having on its surface PNAs as the immobilized biosensor molecule of section i) of the hybridization determination assay, and in which the object of the hybridization is a candidate biological molecule consisting of a natural nucleic acid (DNA or RNA). To that end, another particular aspect of the present invention is formed by the use of the nanoparticle biosensor of the invention in which the determination of hybridization or not in step i) of the hybridization determination assay consists of the hybridization between a PNA molecule immobilized in the nanoparticle biosensor and a DNA molecule present in a test sample.

Another particular embodiment of the invention is a nanoparticle biosensor having on its surface natural antibodies, artificial antibodies, recombinant antibodies or mini-antibodies as the immobilized biosensor molecule of section i) of the hybridization determination assay, and in which the object of the hybridization or binding is the antigen specifically recognized by said antibody. In this case, the antigen must have in its molecular structure functional groups different from those of the protein acting as antibody, such it can be detected by spectroscopic or electrochemical techniques. Said antigen-specific functional groups that are not present in the protein can be, by way of illustration and without limiting the scope of the invention: aliphatic hydrocarbons, aromatic hydrocarbons, heterocycles, D-amino acids, functional groups containing nitrogen, sulfur, phosphorus or metals forming coordination bonds.

Another particular embodiment of the invention is a nanoparticle biosensor having on its surface, as the immobilized biosensor molecule of section i) of the hybridization determination assay, aptamers, ribozymes, aptazymes or other nucleic acids which have been provided with (or enriched in) the capacity to recognize specific ligands and bind specifically to them by means of in vitro selection processes. In this case, the ligand the binding of which can be detected must have in its molecular structure functional groups different from those of the nucleic acid acting as a biosensor molecule, i.e. any group other than the following: ribose, deoxyribose, phosphate, purine or pyrimidine nitrogenated base. Said ligand-specific functional groups can be, by way of illustration and without limiting the scope of the invention: aliphatic hydrocarbons, aromatic hydrocarbons, heterocycles, D-amino acids, functional groups containing nitrogen, sulfur, phosphorus or metals forming coordination bonds.

A preferred embodiment of the present invention is formed by a method of detecting the hybridization of step iii) of the hybridization or binding determination assay carried out by means of spectroscopic detection. The spectroscopic detection measurement can preferably be carried out by means of ultraviolet radiation. The spectroscopic measurement can more preferably be carried out by means of infrared radiation.

In another preferred aspect of the invention, the hybridization detection is carried out by means of Raman spectroscopy.

The Raman and infrared (IR) technique measure in the same region as the electromagnetic radiation spectrum, that of the vibrational energy of the molecules, although both techniques detect different phenomena occurring with chemical bonds. The difference is that IR provides the polarity change signal of the bond excited according to one vibration or another, and Raman provides the polarizability change undergone by the bond. The spectroscopic measurement will provide a series of absorption bands (in the case of IR) or dispersion bands (in the case of Raman) in which the vibration frequencies of the non-common parts between the biosensor molecule immobilized on the nanoparticles and the candidate biological molecule the presence of which is to be detected are searched for. In the case of DNA or RNA detection using PNA immobilized on nanoparticles, these bands correspond to the backbone on which the nucleic bases are arranged, which as already mentioned in the case of PNA is a strand with a peptide nature, and for natural nucleic acids (DNA and RNA) it is of a sugar-phosphate type (2-deoxyribose or ribose, respectively, joined by phosphodiester bonds).

Thus, one particular embodiment of the invention lo is formed by a method of spectroscopically detecting the nucleic acid hybridized on the nanoparticle in the infrared region which is carried out by means of a method, by way of illustration and without limiting the scope of the present invention, belonging to the following group:
  a) by means of using infrared equipment, measuring the absorption of the nanoparticles by transmission
  b) by means of using infrared equipment, measuring the absorption of the nanoparticles by attenuated total reflection (ATR)
  c) by means of the using infrared equipment, measuring the absorption of the nanoparticles in the grazing angle mode.

In one particular embodiment of the invention, the infrared equipment used in the previous section a) is table-top equipment located in a laboratory, integrating the Fourier Transform (FT) technique for spectrum resolution, and using barium fluoride, calcium fluoride transmission windows or any other type of window transparent to infrared radiation, by way of example and without being limited to: potassium bromide, potassium chloride, sodium chloride or sodium bromide. In another particular embodiment of said method, the windows transparent to infrared radiation can adopt a flow configuration whereby successive samples can be analyzed continuously.

In a preferred embodiment of the invention, the infrared equipment used in the previous section a) anterior is portable equipment for analyzing field samples, being able to be Fourier Transform equipment or on the contrary, have a dispersive continuous irradiation system and detector limited to the frequencies of interest.

In a still more preferred embodiment of the invention, in the infrared equipment used in the previous section b), in the attenuated total reflection (ATR) mode, the flow configuration can be adopted with or without the application of an external magnetic field which allows maintaining the magnetic nanoparticles positioned in the cell. In a still more preferred embodiment of the invention, in the infrared equipment used in the previous section b) by means of the attenuated total reflection (ATR) mode in the flow configuration, the thermostatted cell with an external magnetic field can be used. A temperature gradient can thus be used and the effect of said temperature on the stability of the hybridization between the PNA probe immobilized on the nanoparticle and the target nucleic acid (DNA or RNA) can be studied.

In another particular embodiment of the invention, the infrared equipment used in section b) has a zinc selenide window, being able to be substituted with any other crystal suitable for the ATR technique (such as germanium, for example). In another particular embodiment, the crystal suitable for the ATR technique can be coated by a thin gold or silver film.

In another particular embodiment of said method, the nanoparticle biosensors containing PNA probes can be regularly arranged in discrete areas of a surface and after the hybridization step, they can be analyzed by means of infrared microscopy individually or in a microarray arrangement.

Figure 5:
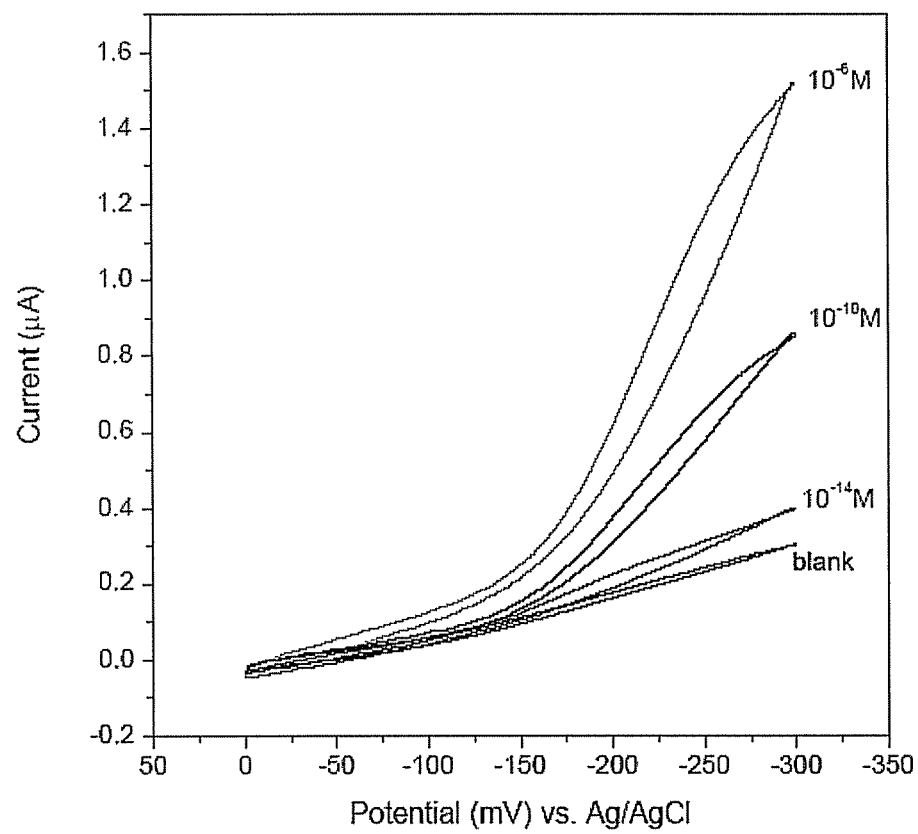
FIG. 5.—Cyclic voltammetries of gold electrodes (disks with a diameter of 3 mm) coated with a thiolated PNA monolayer, incubated in a complementary DNA solution (at the concentrations indicated in the Figure), washed and subsequently incubated in $10^{-6}$ M thionine, $10^{-3}$ M $H_2O_2$ and 0.1 mg/ml peroxidase enzyme.

In addition, the outer metal layer that the nanoparticles have provide them with another property; they can conduct electricity along their surface. This provides them with a nanoelectrode character, being able to transmit an electric signal in solution to an electrode on which the magnetic particles are confined by gravity or by the influence of an external magnetic field. A practical example of this embodiment, carried out on gold disk electrodes, functionalized with a thiolated PNA monolayer, is shown in FIG. 5. Similar results have been obtained with the magnetic nanoparticle biosensors described in this patent.

In one particular embodiment of said method, in section i) of the hybridization determination assay of the invention, the nanoparticles containing immobilized PNA probes are allowed to react with the solution in which the nucleic acid molecules with sequences complementary to said PNA are presumably located. In step ii) of the hybridization determination assay of the invention, the nanoparticles with the hybridized nucleic acid are recovered and incubated in a solution containing a redox compound, i.e. with different properties in its oxidized state and in its reduced state. Said redox compound has an overall positive charge in its oxidized state whereas it has no charge in its reduced state. These compounds, hereinafter referred to as redox mediators, belong, by way of illustration and without limiting the scope of the invention, to the following group: the thionine compound, the methylene blue compound, the bipyridyl-osmium compound or the benzyl viologen compound.

One of the original experimental facts supporting the present invention is that said redox mediators are electrostatically adsorbed on the DNA strands hybridized on complementary PNA strands. However, as has been experimentally observed, after their electrochemical reduction, said redox mediators lose their electric charge and thus their electrostatic affinity for DNA, they are therefore diffused to the medium and can be electrochemically detected. This phenomenon takes place when the PNA/DNA heteroduplexes have been formed on a mass electrode, and also when they have been formed on conductive nanoelectrodes which, deposited on a collector electrode or attracted on it by an external magnetic field, behave as a nanoelectrode array. It has been experimentally determined that the molecules of the redox mediators diffused to the medium can be reduced by the catalytic action of a suitable enzyme (by way of illustration and without limiting the scope of the present invention, a peroxidase enzyme), whereby an amplification effect is obtained (see Example 3).

Therefore, one particular embodiment of the present invention is formed by a method of determining the hybridization of 11i) by means of electroanalytical techniques known as dynamic techniques.

In one particular embodiment of the invention, dynamic techniques belong to the category of electrochemical techniques with controlled potential, being comprised, by way of illustration and without limiting the scope of the invention, in the following group: cyclic and/or linear voltammetry and chronoamperometry. As is accepted by any person skilled in the art, sweep and pulse modes and stationary and rotating electrode modes are variables of these techniques.

In one particular embodiment of the invention, dynamic techniques belong to the category of electrochemical techniques with controlled current, of a small amplitude or a large amplitude. Chronopotentiometry and coulometry are comprised among them, by way of illustration and without limiting the scope of the invention.

In one particular embodiment of the invention, voltammetric techniques belong to the stripping category and its variants: the linear sweep, differential pulse, square-wave differential linear sweep stripping.

In a preferred embodiment of the present invention, the variants of electroanalytical techniques can be carried out, instead of with metal nanoparticles, with metal electrodes as a support for the PNA probes. These electrodes can be, by way of illustration and without limiting the scope of the invention, in the form of: disks, wires, rings, spheres or spheroids.

The examples describe certain embodiments of the present invention in more detail below.

EXAMPLES

Example 1

—Synthesis of the Metalized Magnetic Nanoparticle Biosensors of the Invention

Example 1.1

—Gold Nanoparticle Biosensors

The initial object of this embodiment is to prepare a magnetic suspension formed by cobalt ferrite ($CoFe_2O_4$) nanoparticles with a uniform size, coated with a thin silica layer functionalized with amino groups, plus a final coating with a gold layer (as shown in FIG. 1) on which the thiolated PNA molecules will be chemisorbed as an example of a biosensor molecule. The silica coating takes place on the magnetic nanoparticles individually, also being able to obtain the coating several magnetic cores simultaneously. The nanoparticles thus prepared comply with the properties sought: they are stable in suspension for a long time period, but they sediment in the presence of a magnetic field. Furthermore, by removing said magnetic field, the nanoparticles must be dispersed upon applying a gentle stirring.

In one particular example, cobalt ferrite with an inverse spinel structure has been used, synthesized to a size of 17±3 nm, with suitable magnetic properties ($M_s$=73 emu/g). These nanoparticles are synthesized by co-precipitation of $Fe^{3+}$ and $Co^{2+}$ in a boiling alkaline solution by the Wagner method (Wagner et al., 2002). The nanoparticles thus obtained have an isoelectric point approximately at 8.5, which makes them quite unstable in aqueous solutions with a pH comprised between 7 and 10. The following step consists of coating this ferrofluid with a silica layer, whereby achieving lowering the isoelectric point of the nanoparticles to 3, making them stable in solution at neutral pHs. The silica layer in turn allows subsequently inserting functional groups in order to work on the surface of the nanoparticles.

The nanoparticles are coated with silica as follows: 30 ml of the previously synthesized cobalt ferrite ferrofluid are taken and diluted to 150 ml with water. 500 μL of tetramethylammonium (TMA) hydroxide are later added, the pH increasing to 11.5-12, and are transferred to the reaction flask. 100 ml of sodium silicate in a 0.50% solution are then prepared, and with the previously synthesized Dowex WX8 resin, the pH is decreased to 10.5, after which it is filtered with filter paper to remove the ion exchange resin.

The flask with the ferrofluid is heated to boiling with a reflux system, and the 100 ml of sodium silicate are added throughout 2 hours, dropwise during the first one and a half hours and with the aid of a peristaltic pump. The volume must remain constant, for which some of the vapor is gradually released if necessary. When the reaction ends, it is allowed to air cool to room temperature. The reaction product is dialyzed for four days in cellophane tubes against water, taken to pH=10 by adding two drops of TMA. The dialysis water is changed every day.

To introduce the amino group on the surface of the magnetic nanoparticles that are already coated with silica, a reaction based on the Stöber method (Wang et al., 1996), a condensation of siloxane groups between the silane groups of 3-aminopropyltriethoxysilane (APTES) and the silica layer deposited in the previous step on the ferrofluid, is used. To that end, the suitable amount of absolute ethanol with 1% ammonia, the ferrofluid at 1.5% and APTES at a 1 millimolar (mM) concentration are placed in a reaction flask and allowed to stir gently at 400 revolutions per minute (rpm) and with a glass rod until the next day. The particles are then magnetically sedimented and washed with ethanol, re-dispersing them after two washings in a volume equal to the original amount of ferrofluid. To that end, a brief immersion (between 15 and 20 seconds) in an ultrasound bath is needed.

To take the functionalized ferrofluid to an aqueous phase, the nanoparticles are magnetically sedimented and the ethanol is decanted, being substituted with an equal volume of 20 mM aqueous HEPES solution at pH=12. It is then introduced in an ultrasound bath for the time necessary for a correct dispersion, This method is carried out three times to eliminate all the ethanol.

In a parallel manner, gold nanoparticles are synthesized according to the method of reducing a gold (III) salt, described by D. Duff and A. Baiker (Duff and Baiker, 1993). In this case, a basic solution was prepared with final concentrations of 60 mM for NaOH, 1 mM for the reducing agent [tetrakis(hydroxyphenyl)phosphonium chloride, (THPC)] and 1 mM for $HAuCl_4$. In an aqueous medium, these compounds are added with stirring at 600 rpm, in this order and in the columns corresponding to the final amount which is to be prepared. After the formation of the colloid, occurring a few seconds after adding the gold salt, it is filtered with a Whatman cellulose nitrate filter with a pore size of 450 nm, and it is stored.

The gold nanoparticles are immobilized on the cobalt ferrite ferrofluid functionalized with amino and/or thiol groups on its surface by self-assembly to these functional groups, using the known affinity of these groups for gold, a chemisorption occurring. Specifically, the presence of gold nanoparticles next to the functionalized magnetic nanoparticles leads to the surface decoration of the latter with the former, each magnetic nanoparticle being coated by several gold nanoparticles. These gold nanoparticles are the seed for reducing metals on the surface, favoring the growth of a gold or silver layer on the nanoparticle. This occurs when they are placed in the presence of the metal ions with which the nanoparticle is to be coated and a mild reducing agent which can make a metal surface grow but without cannot cause secondary nucleation.

Given that both dispersions—functionalized cobalt ferrite ferrofluid and the gold nanoparticles—are at a basic pH, both colloids can be mixed without there being subsequent flocculation problems during the self-assembly. Equal amounts of both fluids are added initially, and after homogenizing in a vortex, the mixture is allowed to react for two hours. The nanoparticles are then magnetically sedimented and it is checked by means of spectrophotometry whether there are gold nanoparticles in the supernatant. If there are not any, the sediment is re-dispersed and more gold nanoparticles are added, the process being repeated until the surface of the magnetic nanoparticles is saturated with the gold nanoparticles, at which time a excess of gold will be detected in the supernatant. The particles are then washed by magnetic sedimentation and subsequent re-dispersion in a 20 mM HEPES medium at pH=11 three times, to eliminate the excess of gold nanoparticles.

A gold layer is grown on the previous nanoparticles already decorated with gold nanoparticles by means of the reduction of $HAuCl_4$ with a mild reducer favoring the growth instead of the nucleation of new gold particles, such as hydroxylamine (NH2OH). In each reduction, the magnetic nanoparticles decorated with gold nanoparticles act as nucleation centers. By repeating this reduction process several times, the formation of a continuous gold layer on the magnetic nanoparticles is achieved. Furthermore, according to the amount of gold that is added and the number of reduction steps, different particle sizes can be achieved. This is shown in the surface plasmon resonance absorption band, which shifts according to amount of gold added.

Figure 2:
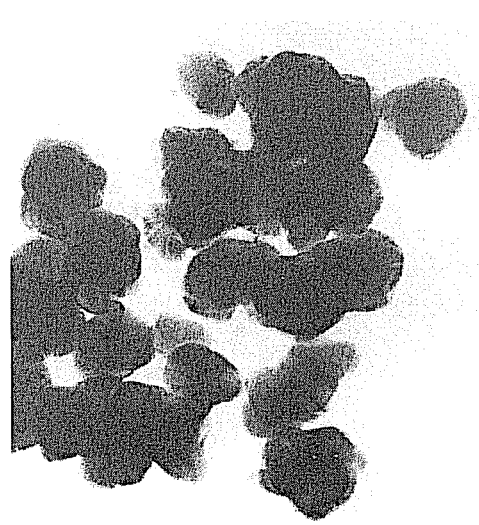
FIG. 2.—Transmission electron microscopy (TEM) image of gold/silica/cobalt ferrite nanoparticles. The image has a 120,000 magnification and the white bar represents 50 nm.

The final size of the nanoparticle biosensors produced in the present example is comprised between 50 and 80 nm in diameter, as can be verified by transmission electron microscopy (FIG. 2). The magnetic particles forming the core of the nanoparticles have 18±3 nm, and the thickness of the silica layer is between 1 and 15 nm.

Example 1.2

—Synthesis of Gold/Silver Alloy Nanoparticle Biosensors

The process of obtaining nanoparticles coated by a Au/Ag alloy is based on reducing silver ion on the magnetic nanoparticles decorated with gold nanoparticles obtained as indicated in section 1.1. To that end, 500 μl of the ferrofluid decorated with gold particles, 400 μl of 0.5 M glycine, 600 μl of water (with Milli-Q purity), 20 W of 12 mM $AgNO_3$ and 100 μl of 10 mM ascorbic acid were placed. This solution is left at room temperature and in darkness for 6 hours, the nanoparticles are washed by magnetic sedimentation three times, re-suspending in 500 μL of water each time, and the process is repeated (Huang et al., 2004). The immobilization of the PNA molecules is carried out as will be detailed in Example 1.4.

Example 1.3

—Synthesis of Gold, Silver and Gold Nanoparticle Biosensors 2 ml of a cobalt ferrite ferrofluid the synthesis of which has been described in Example 1.1. are taken and are reacted with a mixture of two silanes, in different proportions between 50 and 80% of 3-APTES and the rest of 3-MPTMS. The added volume of these reagents adds up to 50 µl. All of this is carried out in a flask, with gentle stirring (100 rpm), with a glass rod, placing 288 ml of absolute ethanol and 10 ml of 25% $NH_3$. The ferrofluid is then poured and finally, the silanes. This is allows to react at room temperature until the next day. They are subsequently washed, re-suspended 2 times in 20 ml of ethanol and another 3 times in water, and are left in a final volume of 10 ml (the nanoparticle concentration is thus diluted 5 times, such that there is approximately 3 mg/ml).

In addition, gold nanoparticles are synthesized according to the method described in section 1.1.

The gold nanoparticles are placed in the presence of the functionalized magnetic nanoparticles and the suspension is acidified such that the gold is immobilized on the ferrofluid, for at least one hour. It is then washed and upon re-suspending in 5 ml of water, the pH is increased up to 11 with 1N NaOH. At this point, upon attracting with a magnet, no gold must remain in the solution.

It is then coated with silver according to the formaldehyde method described by N. Halas (Hallas et al., 2005), which step is carried out the number of times necessary for achieving a complete coating. The method consists of taking 9 ml of water with a 0.15 mM concentration of AgNO3 and adding 500 µL of the magnetic nanoparticles decorated with gold. 50 µL of 37% formaldehyde are then added, it is quickly stirred with the vortex and 50 µL of 25% NH3 are immediately poured. It is stirred again and after two minutes, it is magnetically sedimented. The plasmon of the supernatant is measured, and after washing twice, the plasmon of the nanoparticles is measured. These measurements are carried out in all the coating steps, until it can be seen that the plasmon of the silver extends along the entire visible range, at which point it is considered that the silver layer is virtually closed.

The silver layer is in turn subsequently coated with gold by the method described in Example 1.1., re-suspending until a greater dilution: 0.3 mg/ml instead of 3 mg/ml. The final result is that the nanoparticles acquire a higher stability in solution, and do not aggregate. Three gold coating steps are placed in the following conditions: 5 ml of nanoparticles at 0.3 mg/ml, 50 µL of 25 mM $HAuCl_4$ and 80 µL of 100 mM $NH_2OH.HCl$, with stirring in the vortex. It is washed twice, and the coating steps are tracked with the variation of the surface plasmon resonance band. It is observed how the band at 520 nm grows, and the maximum shifts towards longer wavelengths, which indicates the progress of the coating. When the nanoparticles are coated 10 times more diluted, as in this case, their stability is much higher.

Example 1.4

—Immobilization of PNA on the Nanoparticle Biosensors with an Outer Gold or Silver Layer After that indicated in Examples 1.1 to 1.3, a biosensor molecule is immobilized in the magnetic nanoparticles coated with gold thus prepared. Specifically for the present example, a PNA type organic molecule has been used, which provides the nanoparticle biosensor of the invention with the functionality of being able to hybridize to natural nucleic acids (DNA or RNA) with sequences complementary to those of PNA. The outer gold layer of the nanoparticles has support properties, and thiolated compounds can be chemisorbed on it. The PNAs which will be immobilized on the nanoparticles therefore have at one end a thiol group provided by a cysteine (Cys), such that they will form oriented PNA strand monolayers, as previously shown by the inventors with gold crystals (Briones et al., 2004; 2005).

In particular embodiments of this example, two different single stranded PNA molecules have been used, both of them with a cysteine at their amino end. After the Cys, the PNA molecules have two "O" type spacer groups corresponding to 8-amino-3,6-dioxaoctanoic acid molecules, and together forming a spacer with a length of 3 nm which allows separating the end of the molecule immobilized on the nanoparticle from the sensor region which can bind to nucleic acids. The first PNA molecule used is called "P-G", it has a length of 11 nucleotide bases and its sequence (written from the amino end to the carboxyl end) is: Cys-O—O-SEQ ID NO. 1. This sequence has been chosen due to its relevance in animal virology, because it corresponds to the most antigenic region (called "ROD loop") of the VP1 protein of the foot and mouth disease virus (FMDV) capsid (Martínez et al., 1997).

The second PNA sequence is called "P-M" and its sequence (with a length of 9 nucleotide bases) is: Cys-O—O-SEQ ID NO. 2. This sequence has been chosen due to its biosanitary relevance, because it includes the sequence complementary to codon 41 of the reverse transcriptase (RT) region of the pol gene of the human immunodeficiency virus (HIV), a position in which the frequent appearance of the M41 L mutation involved in the HIV resistance of the antiviral drug called Zidovudine (AZT) has been described (Yeni et al., 2002).

To immobilize PNA on the nanoparticles, 76 µL of the previously prepared ferrofluid coated with gold are taken and 4 µL of a PNA molecule solution diluted in water (Milli-Q purity) at a 10 µM concentration are added at a temperature between 20 and 25° C., for three and a quarter hour. The nanoparticles are then magnetically sedimented and the supernatant is changed for water. The nanoparticles are resuspended and the process is repeated twice more to remove all the PNA that has not reacted with the gold coating of the nanoparticles. The nanoparticles already decorated with PNA are concentrated under the action of a magnetic field and the adsorption of the PNA molecules is checked by transmission infrared spectroscopy (dotted line in FIG. 3). This spectrum of PNA on the nanoparticle will be considered the "blank" in the subsequent experiments of hybridization of the nanoparticles to DNA of a sample, as described in Example 2.

Example 2

—Hybridization of the Nanoparticle Biosensor Coated with Gold and PNA to a DNA Molecule with a Sequence Complementary to that of PNA. Determination by Means of Increasing the Intensity of the Infrared Absorption Bands Due to the Hybridization of DNA with PNA As indicated previously, the most important structural difference between PNA and natural nucleic acids is that the former has a backbone with a peptide nature whereas the backbone of DNA and RNA have a succession of deoxyribose (DNA) or ribose (RNA) and phosphate groups (Nielsen et al., 1991; Egholm et al., 1992). Therefore, PNA lacks phosphate groups and glucoside rings, which offers a special utility in the design of biosensors for detecting DNA or RNA hybridization. In this example, the fact that the most notable change caused by PNA/DNA hybridization in the infrared region is provided by the DNA phosphate groups, since they have the antisymmetrical tension (a wide band in the 1260-1200 cm$^{-1}$ range) and the symmetrical tension of the P=O bond (around 1100 cm$^{-1}$) is precisely used. Other spectral facts that can be attributed to the deoxyribose or ribose moieties of the DNA/RNA strands are detected at 1065 cm$^{-1}$. These bands are observed in an area of the spectrum in which neither the PNA and DNA nucleotide bases nor the PNA peptidomimetic backbone absorb radiation. Furthermore, there is an increase in the signal around 1580 cm$^{-1}$ due to the pairing of the nitrogenated bases (See FIGS. 3 and 4).

In the present example, magnetic nanoparticles coated with gold functionalized with "P-G" or with "P-M" PNA molecules, the sequences of which are indicated in Example 1.4, have been used, single stranded DNA molecules having a central region complementary to that of said PNAs have been designed. Four target DNA molecules with a length of 31 nucleotides (nt) have been designed and synthesized, corresponding to the wild type and mutant sequences of FMDV ("DNA-G" 5'-SEQ ID NO. 3-3', and "DNA-E" 5'-SEQ ID NO. 4-3', respectively, differing in the G→A "transition" type mutation in their central position) and of HIV ("DNA-M" 5'-SEQ ID NO. 5-3', and "DNA-L" 5'-SEQ ID NO. 6-3', respectively, differing in the A→T "transversión" type mutation in their central position). The capacity of each family of nanoparticles functionalized with a type of PNA to not only detect the presence of complementary DNA or RNA in a sample but even to discriminate between DNA or RNA sequences with a point mutation is thus studied. This biosensor system is thus applied in the animal and human biosanitary field, both for detecting DNA/RNA sequences characteristics of pathogen viruses and for determining whether said sequences inform of the existence of a viral population which can evade the immune system, escape from vaccines or be resistant to antiviral drugs. In each case, the DNA sequences of the other family are used as a non-hybridization control, i.e. those hybridizations which must not occur (or if they occur, must be completely washed) because the PNA/DNA complementarity sequence is negligible (for example, PNA "P-G" with DNAs "DNA-M" and "DNA-L").

In addition, two single stranded DNA molecules with a length of 20 nt have been designed and synthesized which are in turn complementary to the two PNAs used in either orientation: "DNA-GM": 5'-SEQ ID NO. 7-3' (hybridization parallel to "P-G" and antiparallel to "P-M") and "DNA-MG": 5'-SEQ ID NO. 8-3' (hybridization antiparallel to "P-G" and parallel to "P-M"). Therefore, each of these two DNA molecules can hybridize with the two PNAs coating respective different nanoparticles.

In all cases, the hybridization of the nanoparticles coated with PNA and DNA is carried for 1 hour, at temperatures comprised between 41 and 58° C., with DNA concentrations of 100 µM, and followed by washing of two 15-minute cycles at temperatures comprised between 37 and 50° C. The hybridization solutions (HS) and washing solutions (WS) have been of two types: i) HS formed by 7 mM NaCl+0.7 mM Na citrate (pH=7.2), WS formed by 45 mM NaCl+4.5 mM Na citrate (pH=7.0); ii) HS and WS formed by 60 mM NaCl+6 mM Na citrate+0.72% lauryl sarcosine. Before the analysis, in all cases, a final washing in (Milli Q) water was carried out to remove salt residues.

Figure 3:
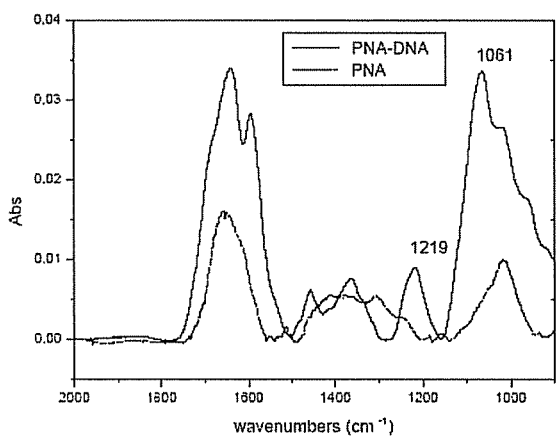
FIG. 3.—Transmission spectra in the infrared area of magnetic nanoparticles with an outer gold layer on the surface of which a thiolated PNA layer with a known sequence ("P-G", see Example 1) has been chemisorbed, and the same preparation after being incubated in the presence of a complementary DNA molecule ("DNA-G", see Example 2) and washed to eliminate the possible non-specific hybridizations.

As an example of the results produced, the infrared spectrum obtained after the hybridization and washing of the nanoparticle biosensors with gold metal coating and coated by "P-G" type PNA with "DNA MG" is shown as a continuous line in FIG. 3. In it, it is obvious that after the hybridization between PNA and perfectly complementary DNA, there appear, among others, the peaks corresponding to the DNA phosphate group, as a signal clearly indicating the hybridization event occurred, at a frequency 1220 and 1060 cm$^{-1}$.

Figure 4:
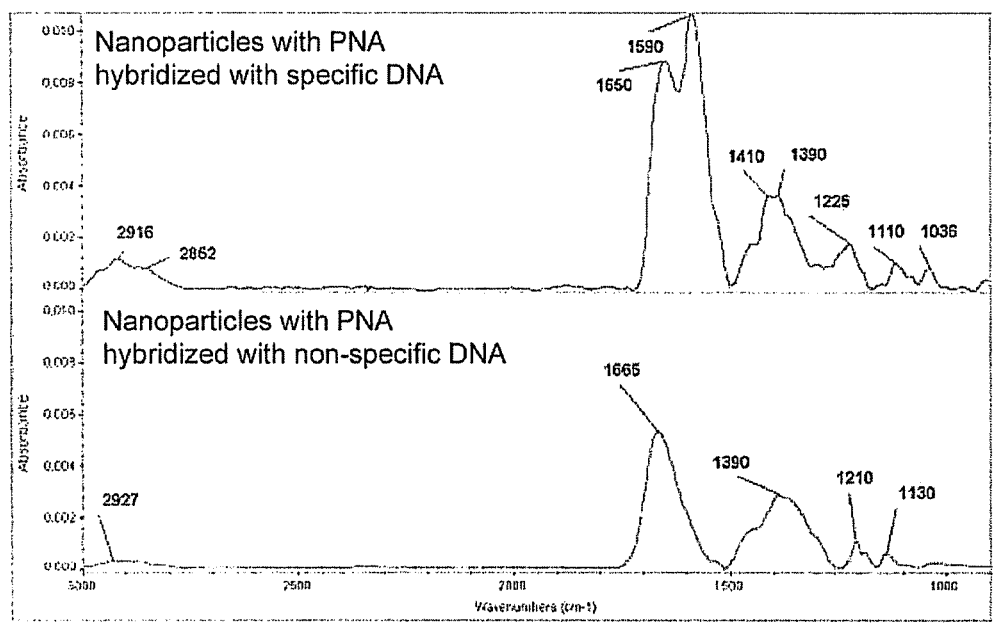
FIG. 4.—Transmission spectra in the infrared area of magnetic nanoparticles with an outer gold-silver-gold layer on the surface of which a thiolated PNA layer with a known sequence "P-G" (see Example 1) has been chemisorbed. In the upper spectrum, these nanoparticles have been incubated with the complementary DNA, "DNA MG", resisting the washing cycle and remaining hybridized, showing their characteristic bands in IR. In the lower spectrum, the nanoparticles have been incubated with a non-specific DNA, "DNA L", that does not hybridize to PNA and is therefore completely eliminated in the washing cycle; the IR bands observed at the end of the process are thus only those characteristic of PNA (see Example 2).

As an example of the results obtained with nanoparticle biosensors with a gold coating formed by successive gold/silver/gold layers, the upper panel of FIG. 4 shows the infrared spectrum obtained after the hybridization and washing of these nanoparticle biosensors coated by "PG" type PNA with "DNA MG" with the complementary sequence. By comparison, the lower spectrum corresponds to nanoparticles identical to the previous ones (coated by "P-G" type PNA) but hybridized with a DNA probe with a sequence that is complementary to PNA ("DNA L"), which, as it is not specifically hybridized, is removed during the washing cycle. The upper spectrum of the figure shows the peaks at 1225 and 1036 cm$^{-1}$ corresponding to the DNA phosphate groups, slightly shifted with respect to their positions in FIG. 3 due to the effect of the silver layer. Furthermore, analogously to that observed in FIG. 3, another spectral fact characteristic of the hybridization of PNA to a complementary DNA is the band at 1590 cm$^{-1}$, corresponding to the specific pairing of the nitrogenated bases of PNA with those of DNA.

Example 3

—Hybridization of the Nanoparticle Biosensor Coated with Gold and PNA to a DNA Molecule with a Sequence Complementary to that of PNA. Cyclic Voltammograms of Thionine Incorporated Through Ionic Interactions with the Phosphate Moieties of DNA Strands The process indicated in Example 2 has been carried out using the nanoparticle biosensors prepared as detailed in Example 1, but using a different hybridization detection technique. Cyclic voltammograms have been obtained using flat gold electrodes modified with the PNA molecules indicated in Example 1.4, subsequently incubated with different concentrations of complementary DNA In this case, after the hybridization and the washing, the hybridized nanoparticles are incubated with a thionine solution and are subjected to a cyclic voltammetry in the presence of peroxidase and $H_2O_2$.

FIG. 5 shows the currents obtained using functionalized nanoparticles with the "P-M" PNA, in a concentration range of "DNA-M" between $10^{-14}$ and $10^{-6}$ M. Subsequent sensitivity increases are obtained by decreasing the reaction volume, whereby detection sensitivities of $10^{-16}$ M of DNA, i.e., of 0.1 femtomolar, are reached.

Literature
1. Abad, J M. Vélez, M., Santamaría, C., Guisan, J. M., Matheus, P. R., Vázquez, L., Gazaryan, I., Gorton, L., Gibson, T. & Fernandez, V. M. Immobilization of peroxidase glycoprotein on gold electrodes modified with mixed epoxy-boronic acid monolayers. J. Am. Chem. Soc. 124, 12845-12853 (2002).
2. Arlinghaus H F, Ostrop M, Friedrichs O, Feldner J C. Genome diagnostics with TOF-SIMS. Appl. Surf. Sci. 203: 689-692 (2003).
3. Arlinghaus, H. F., Kwoka, M. N., Jacobson, K. B. Analysis of biosensor chips for identification of nucleic acids. Anal Chem. 69: 3747-3753 (1997).
4. Brandt, O., Feldner, J., Stephan, A., Schroder, M., Schnolzer, M., Arlinghaus, H. F., Hoheisel, J. D. & Jacob, A. PNA microarrays for hybridisation of unlabelled DNA samples. Nucleic Acids Res. 31, e119-e127 (2003).
5. Briones, C., Mateo-Martí, E., Gómez-Navarro, C., Parro, V., Román, E. and Martín-Gago, J. A. Ordered self-assembled monolayers of peptide nucleic acids with DNA recognition capability. Physical Review Letters 93:208103 (2004).
6. Briones, C., Mateo-Martí, E., Gómez-Navarro, C., Parro, V., Román, E. and Martín-Gago, J. A. Structural and functional characterization of self-assembled monolayers of peptide nucleic acids and its interaction with complementary DNA. Journal of Molecular Catalysis 228: 131-136 (2005).
7. del Monte, F., Morales, M. P., Levy, D., Fernández, A., Ocaña, M., Roig, A., Molins, E. & Serna, C. J. Formation of gamma-Fe2O3 isolated nanoparticles in a silica matrix. Langmuir 13: 3627-3634 (1997).
8. Demidov V V, Protozanova E, Izvolsky K I, Price C, Nielsen P E, Frank-Kamenetskii M D. Kinetics and mechanism of the DNA double helix invasion by pseudocomplementary peptide nucleic acids. Proc Natl Acad Sci USA. 99: 5953-5958 (2002).
9. Demidov V V, Yavnilovich M V, Belotserkovskii B P, Frank-Kamenetskii M D, Nielsen P E. Kinetics and mechanism of polyamide ("peptide") nucleic acid binding to duplex DNA. Proc Natl Acad Sci USA. 92: 2637-2641 (1995).
10. Duff, D. G., Baiker, A. & Edwards, P. P. A new hydrosol of gold clusters. 1. Formation and particle-size variation. Langmuir 9: 2301-2309 (1993).
11. Egholm, M., Buchardt, O., Christensen, L., Behrens, C., Freier, S. M., Driver, D. A., Berg, R. H., Kim, S. K., Norden, B. & Nielsen, P. E. PNA hybridizes to complementary oligonucleotides obeying the Watson-Crick hydrogen-bonding rules. Nature 365, 566-568 (1993).
12. Egholm, M., Buchardt, O R., Nielsen, P. E., & Berg, R. H. Peptide nucleic acids (PNA). Oligonucleotide analogues with an achiral backbone. J. Am. Chem. Soc. 114, 1895-1898 (1992).
13. Garcell L., Morales M. P., Andres-Verges M., Tartaj P. & Serna C. J. Interfacial and rheological characteristics of maghemite aqueous suspensions. J. of Colloid and Interf. Sci. 205, 470-475 (1998).
14. Griffin T J, Tang W, Smith L M. Genetic analysis by peptide nucleic acid affinity MALDI-TOF mass spectrometry. Nat. Biotechnol. 15: 1368-1372 (1997).
15. Hacia, J. G. Resequencing and mutational analysis using oligonucleotide microarrays. Nature Genetics 21: 42-47 (1999).
16. Halas N. Playing with plasmons. Tuning the optical resonant properties of metallic nanoshells. MRS Bulletin 30: 362-367 (2005).
17. Harris, H. The DNA microarray. The Scientist 19: 27-31 (2005).
18. Huang. C. C., Yang, Z. S. & Chang, H. T. Synthesis of dumbbell-shaped Au—Ag core-shell nanorods by seedmediated growth under alkaline conditions. Langmuir 20:6089-6092 (2004).
19. Jackson J B, Halas N J. Silver nanoshells: Variations in morphologies and optical properties. JOURNAL OF PHYSICAL CHEMISTRY B 105: 2743-2746 (2001).
20. Jolivet, J. P., Massart, R. & Fruchard, J. M. Synthesis and physicochemical study of non-surfactant magnetic colloids in an aqueous medium. Nouv. J. Chim. 7: 325-331 (1983).
21. Kambhampati D, Nielsen P E, Knoll W. Investigating the kinetics of DNA-DNA and PNA-DNA interactions using surface plasmon resonance-enhanced fluorescence spectroscopy. Biosens Bioelectron. 16: 1109-1118 (2001).
22. Lee, J., Isobe, T. & Senna, M. Preparation of ultrafine Fe3O4 particles by precipitation in the presence of PVA at high pH. J. Colloid Interface Sci. 177: 490-494 (1996).
23. Madoz, J., Kuznetzov, B. A., Medrano, F. J., García, J. L. & Fernández, V. M. Functionalization of gold surfaces for specific and reversible attachment of a fused beta-galactosidase and choline-receptor protein. J. Am. Chem. Soc. 119: 1043-1051 (1997).
24. Martínez, M. A., Verdaguer, N., Mateu, M. G. & Domingo, E. Evolution subverting essentiality: dispensability of the cell attachment Arg-Gly-Asp motif in multiply passaged foot-and-mouth disease virus. Proc. Natl. Acad. Sci. USA 94, 6798-6802 (1997).
25. Massart, R & Cabuil, V. Effect of some parameters on the formation of colloidal magnetite in alkaline-medium—yield and particle-size control. J. Chem. Phys. 84, 967-973 (1987).
26. Massart, R. Preparation of aqueous magnetic liquids in alkaline and acidic media. IEEE transactions on magnetics 17: 1247-1248 (1981).
27. Nielsen P E. Applications of peptide nucleic acids. Curr Opin Biotechnol. 10: 71-75 (1999).
28. Nielsen P E. Peptide nucleic acid targeting of double stranded DNA. Methods Enzymol. 340: 329-340 (2001).
29. Nielsen, P. E., Egholm, M., Berg, R. H. & Buchardt, O, Sequence-selective recognition of DNA by strand displacement with a thymine-substituted polyamide. Science 254, 1497-1500 (1991).
30. Oldenburg, S. J., Averitt, R. D., Wescott, S. L. & Halas, N. J. Nanoengineering of optical resonances. Chemical Physics Lett. 288: 243-247 (1998).
31. Osawa, M. & Ikeda, M. Surface-enhanced infraredabsorption of para-nitrobenzoic acid deposited on silver island films—contributions of electromagnetic and chemical mechanisms. J. Phys. Chem. 95: 9914-9919 (1991).
32. Parinov, S., Barsky, V., Yershov, G., Kirillov, E., Timofeev, E., Belgovskiy, A. & Mirzabekov, A. DNA sequencing by hybridisation to microchip octa- and decanucleotides extended by stacked pentanucleotides. Nucleic Acids Res. 24, 2998-3004 (1996).
33. Philipse, A. P., van Bruggen, M. P. B. & Pathmamanoharan, C. Magnetic silica dispersions—preparation and stability of surface-modified silica particles with a magnetic core. Langmuir 10: 92-99 (1994).
34. Relógio, A., Schwager, C., Richter, A., Ansorge, W. & Valcárcel, J. Optimization of oligonucleotide-based DNA microarrays. Nucleic Acids Res. 30: e51 (2002).
35. Rogers F A, Vasquez K M, Egholm M, Glazer P M. Sitedirected recombination via bifunctional PNA-DNA conjugates. Proc Natl Acad Sci USA 99: 16695-16700 (2002).
36. Solinas S., Piccaluga G., Morales M. P. & Serna C. J. Sol-gel formation of gamma-Fe2O3/SiO2 nanocomposites; Acta Materialia 49, 2805-2811 (2001).
37. Southern E. M. Detection of specific sequences among DNA fragments separated by gel electrophoresis. J Mol. Biol. 98: 503-517 (1975).
38. Southern E M. Case-Green, S. C., Elder, J. K., Jonson, M., Mir, K. U., Wang, L. & Williams, J. C. Arrays of complementary oligonucleotides for analysing the hybridization behavior of nucleic acids. Nucleic Acids Res. 22: 1368-1373 (1994).

39. Sugimoto, T. & Matijevic, E. Formation of uniform spherical magnetite particles by crystallization from ferrous hydroxide ges. J. Colloid Interface Sci. 74:227-243 (1980).
40. Tartaj, P., González-Carreño, T. & Serna, C. J. Single-step nanoengineering of silica coated maghemite hollow spheres with tunable magnetic properties. Advanced materials 13: 1620-1624 (2001).
41. Urakawa, T., Nakzawa, T., Inoue, H., Shirat, T. & Fluk, E. J. Preparation and Mossbauer spectroscopic characterization of ultrafine iron oxide particles. J. Mater. Sci. Lett. 15: 1237-1239 (1996).
42. Veintenillas-Verdaguer, S., Morales, M. P. & Serna, C. J. Continuous production of gamma $Fe_2O_3$ ultrafine powders by laser pyrolysis. Materials Lett. 35, 227-231 (1998).
43. Vo-Dinh, T. Surface-enhanced Raman spectroscopy using metallic nanostructures. Trends in Anal. Chem. 17: 557-582 (1998).
44. Wagner, J., Autenrieth, T. & Hempelmann, R. Core shell particles consisting of cobalt ferrite and silica as model ferrofluids [$CoFe_2O_4$—$SiO_2$ core shell particles]. J. of Magnetism and Magnetic Materials 252: 4-6 (2002).
45. Wang J, Nielsen P E, Jiang M, Cai X, Fernandes J R, Grant D H, Ozsoz M, Beglieter A, Mowat M. Mismatch-sensitive hybridization detection by peptide nucleic acids immobilized on a quartz crystal microbalance. Anal Chem. 69: 5200-5202 (1997).
46. Wang, J., Palecek, E., Nielsen, R E., Rivas, G., Cai, X., Shiraishi, H., Dontha, N., Luo, D., Farias, P. A. M. Peptide Nucleic Acid Probes for Sequence-Specific DNA Biosensors. J. Am. Chem. Soc. 118: 7667-7670 (1996).
47. Watson, J. D. & Crick, H. D. Molecular Structure of Nucleic Acids: A Structure for Deoxyribose Nucleic Acid. Nature 171: 737-738 (1953).
48. Wittung, P., Nielsen, P. E., Buchardt, O., Egholm, M. & Norden, B. DNA-like double helix formed by peptide nucleic acid. Nature 368: 561-563 (1994).
49. Yeni, P. G., Hammer, S. M., Carpenter, C. C., Cooper, D. A., Fischl, M. A., Gatell, J. M., Gazzard, B. G., Hirsch, M. S., Jacobsen, D. M., Katzenstein, D. A., Montaner, J. S., Richman, D. D., Saag, M. S., Schechter, M., Schooley, R. T., Thompson, M. A., Vella, S. & Volberding, P. A. Antiretroviral treatment for adult HIV infection in 2002: updated recommendations of the International AIDS Society-USA Panel. JAMA 288, 222-235 (2002).

The invention claimed is:

1. A nanoparticle biosensor comprising:
   a. a magnetic core comprising cobalt ferrite;
   b. a silica layer which surrounds the magnetic core, wherein the silica layer comprises amino groups or thiol groups;
   c. an outer metal layer which surrounds the silica layer, wherein the outer metal layer comprises a gold layer, or a silver layer covered by an additional gold layer; and
   d. a peptide-nucleic acid (PNA) immobilized onto the outer metal layer.

2. The nanoparticle biosensor of claim 1, wherein:
the magnetic core has a diameter of 4 nm to 30 nm;
the silica layer has a thickness of 1 nm to 20 nm; and
the outer metal layer has a thickness of 1 nm to 200 nm.

3. A method of preparing the nanoparticle biosensor of claim 1, comprising the steps of:
   a. preparing a colloid of magnetic particles comprising cobalt ferrite, the magnetic particles having a diameter between 4 nm and 30 nm,
   b. conditioning the colloid so that it is stable at a pH greater than 7;
   c. coating the magnetic particles with silica in a basic medium to form a silica layer surrounding the magnetic particles, the silica layer having a thickness between 1 nm and 20 nm;
   d. chemically functionalizing the surface of the coated magnetic particles obtained in step c) to introduce amino or thiol groups;
   e. further coating the functionalized magnetic particles of step d) with a metal layer, the metal layer comprising a gold layer or a silver layer covered by an additional gold layer;
   f. immobilizing a biosensor molecule comprising a peptide-nucleic acid (PNA) on the surface of the magnetic particle resulting from step e).

4. The method of claim 3, wherein the step e) comprises the following sub-steps:
   i. synthesizing water-stable metal nanoparticles having a diameter between 3 and 20 nm,
   ii. chemisorbing the metal nanoparticles on the resulting magnetic particles of step d), and
   iii. growing a metal layer on the product obtained in sub-step (ii) and controlling the thickness of the metal layer between 1 and 200 nm.

5. The method of claim 3, wherein the step c) comprises forming the silica layer comprising tetraethoxyorthosilicate.

6. A method of preparing a microarray or a micromatrix comprising forming a microarray or micromatrix wherein each point of the microarray or the micromatrix comprises a nanoparticle biosensor according to claim 1.

7. A method of using the nanoparticle biosensor according to claim 1 for at least one of the following applications:
   a. detection of viral, bacterial, fungal or protozoan type pathogens
   b. characterization of mutations or genetic polymorphisms (SNPs) in said agents which can make them resistant to drugs or facilitate the escape from vaccines, c. characterization of mutations or SNPs in human or animal genes related to diseases or prone to them,
d. detection of specific tumor markers,
e. detection of specific microorganisms, pathogens or contaminants in food,
f. detection of the presence of transgenic or genetically modified organisms (GMOs) in food,
g. detection of microorganisms or toxins contaminating the environment.

8. A method of determining existence or absence of a biological molecule in a sample, comprising the steps of:
a. reacting a nanoparticle biosensor according to claim 1 with the sample;
b. capturing the nanoparticle biosensor by magnetic sedimentation,
c. determining whether hybridization occurred in step a),
d. deducing existence of the biological molecule in the sample if hybridization occurred in step a);
e. optionally quantifying concentration of the biological molecule in the sample.

9. The method of claim 8, wherein the step c) comprises spectroscopic detection.

10. The method of claim 9, wherein the spectroscopic detection uses ultraviolet radiation.

11. The method of claim 9, wherein the spectroscopic detection uses visible radiation.

12. The method of claim 9, wherein the spectroscopic detection uses infrared radiation.

13. The method of claim 12, wherein the spectroscopic detection comprises measuring the absorption of the nanoparticles by transmission or attenuated total reflection or in the grazing angle mode.

14. The method of claim 13, wherein the measurement of the absorption of the nanoparticles by transmission integrates the Fourier Transform technique for the resolution of spectra and uses barium fluoride or calcium fluoride transmission windows or another type of window transparent to infrared radiation.

15. The method according to claim 14, wherein the windows transparent to infrared radiation adopt a flow configuration.

16. The method of claim 9, wherein the spectroscopic detection comprises detection using Raman spectroscopy.

17. A method for detecting an electrochemical probe which is carried out by means of linear, cyclic or pulse electrochemical techniques, which probe is electrostatically attracted by the negative charges carried by DNA and RNA strands hybridized with neutral PNA strands immobilized on the nanoparticle biosensor of claim 1.

18. The method of claim 17, wherein the electrochemical probe is a molecule that is cationic in its oxidized state or neutral or anionic in its reduced state.

19. The method of claim 18, wherein the electrochemical probe in its neutral or negatively charged state can be catalytically re-oxidized to its positive charge state by an enzyme or another catalyst.

20. The method of claim 19, wherein the catalyst obtains electrons from the electrochemical probe and transfers them to a suitable reagent.

21. The method according to claim 20, wherein the reagent is hydrogen peroxide.

22. The method according to claim 19, wherein the enzyme is a peroxidase.

23. The method according to claim 19, wherein the probe is the thionine molecule.

* * * * *

```
SEQUENCE LISTING

<160> NUMBER OF SEQ ID NOS: 8

<210> SEQ ID NO 1
<211> LENGTH: 11
<212> TYPE: DNA
<213> ORGANISM: Artificial Sequence
<220> FEATURE:
<223> OTHER INFORMATION: synthetic construct - the sequence corresponds
      to the 11 nucleotide bases located starting from Cys-O-O- and
      located on the PNA backbone.

<400> SEQUENCE: 1
aatccccgca t                                                           11

<210> SEQ ID NO 2
<211> LENGTH: 9
<212> TYPE: DNA
<213> ORGANISM: Artificial Sequence
<220> FEATURE:
<223> OTHER INFORMATION: synthetic construct - the sequence corresponds
      to the 9 nucleotide bases located starting from Cys-O-O- and
      located on the PNA backbone.

<400> SEQUENCE: 2 gccatctct                                                               9

<210> SEQ ID NO 3
<211> LENGTH: 31
<212> TYPE: DNA
<213> ORGANISM: Foot-and-mouth disease virus

<400> SEQUENCE: 3
ccgccagtgc atgcggggat ttggctcacc t                                     31

<210> SEQ ID NO 4
<211> LENGTH: 31
<212> TYPE: DNA
<213> ORGANISM: Foot-and-mouth disease virus

<400> SEQUENCE: 4
ccgccagtgc atgcgaggat ttggctcacc t                                     31
```

```
<210> SEQ ID NO 5
<211> LENGTH: 31
<212> TYPE: DNA
<213> ORGANISM: Human immunodeficiency virus

<400> SEQUENCE: 5
gaaatttgta cagagatgga aaaggaaggg a                              31

<210> SEQ ID NO 6
<211> LENGTH: 31
<212> TYPE: DNA
<213> ORGANISM: Human immunodeficiency virus

<400> SEQUENCE: 6
gaaatttgta cagagttgga aaaggaaggg a                              31

<210> SEQ ID NO 7
<211> LENGTH: 20
<212> TYPE: DNA
<213> ORGANISM: Artificial Sequence
<220> FEATURE:
<223> OTHER INFORMATION: synthetic construct - probe

<400> SEQUENCE: 7 ttagggcgt aagagatggc                                            20

<210> SEQ ID NO 8
<211> LENGTH: 20
<212> TYPE: DNA
<213> ORGANISM: Artificial Sequence
<220> FEATURE:
<223> OTHER INFORMATION: synthetic construct - probe

<400> SEQUENCE: 8
cggtagagaa tgcggggatt                                           20
```